US012658309B2

(12) United States Patent
Chang et al.

(10) Patent No.: US 12,658,309 B2
(45) Date of Patent: Jun. 16, 2026

(54) METHODS AND SYSTEMS FOR PATIENT DISCHARGE MANAGEMENT

(71) Applicant: GE Precision Healthcare LLC, Wauwatosa, WI (US)

(72) Inventors: Jehoshua Joon Chang, Suwanee, GA (US); Jeffrey R Terry, Plano, TX (US); Bex George Thomas, San Ramon, CA (US); Kathleen P Martin, Pinckney, MI (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 596 days.

(21) Appl. No.: 17/804,940

(22) Filed: Jun. 1, 2022

(65) Prior Publication Data

US 2023/0395241 A1    Dec. 7, 2023

(51) Int. Cl.
*G16H 40/20* (2018.01)
*G06N 5/022* (2023.01)
*G16H 10/60* (2018.01)

(52) U.S. Cl.
CPC ............. *G16H 40/20* (2018.01); *G06N 5/022* (2013.01); *G16H 10/60* (2018.01)

(58) Field of Classification Search
CPC ......... G16H 40/20; G16H 10/60; G06N 5/022
See application file for complete search history.

(56) References Cited

U.S. PATENT DOCUMENTS 11,348,689 B1 *  5/2022  Gonzales, Jr. ......... G16H 10/60
11,908,573 B1 *  2/2024  Forehand ............... G16H 10/60

| | | | |
|---|---|---|---|
| 2009/0043707 A1 | 2/2009 | Roberts | |
| 2016/0180029 A1* | 6/2016 | Shanbhag .............. | G16H 10/60 705/3 |
| 2016/0321404 A1* | 11/2016 | Ginsburg ............... | G16H 10/60 |
| 2020/0211692 A1* | 7/2020 | Kalafut .................. | G16H 30/40 |
| 2020/0258618 A1 | 8/2020 | Zhou | |
| 2021/0098090 A1* | 4/2021 | Thomas ................. | G16H 50/30 |
| 2021/0375437 A1 | 12/2021 | Vasudevan | |

(Continued)

OTHER PUBLICATIONS

Chris Piech, K Means, Stanford CS221 (available online at https://stanford.edu/~cpiech/cs221/handouts/kmeans.html (Year: 2013).*

(Continued)

*Primary Examiner* — Jordan L Jackson

(74) *Attorney, Agent, or Firm* — McCoy Russell LLP

(57) ABSTRACT

Various methods and systems are provided for predicting a discharge date of a patient of a healthcare facility. In one embodiment, a method for a patient management system of a healthcare facility comprises receiving a selected confidence level from a user of the patient management system; predicting a date for discharging a patient of the healthcare facility using a trained discharge date prediction model, based on a set of patient data of the patient, the discharge date prediction model trained on historical patient data of the healthcare facility; based on the received confidence level and an output of the trained discharge date prediction model, predict a discharge date window of the patient; generating a predicted discharge date window element summarizing the discharge window prediction in a user interface (UI) of the patient management system; and displaying the UI on a display device of the patient management system.

18 Claims, 10 Drawing Sheets

(56) References Cited

U.S. PATENT DOCUMENTS

| | | | |
|---|---|---|---|
| 2021/0391062 A1* | 12/2021 | Bhavani ................. | G16H 40/20 |
| 2022/0336088 A1* | 10/2022 | Thomas ................. | G16H 50/20 |
| 2022/0374735 A1* | 11/2022 | Rathod .............. | G06F 16/9024 |
| 2023/0253100 A1* | 8/2023 | Caudill ................... | G06N 3/09 |
| | | | 705/3 |

OTHER PUBLICATIONS

El-Darzi et al., Length of Stay-Based Clustering Methods for Patient Grouping, Intelligent Patient Management 39-56 (Year: 2009).*
Shea et al., An Introduction to Convolutional Neural Networks, arXiv:1511.08458 (Dec. 2, 2015) (Year: 2015).*
Hironori Uematsu et al., Prediction model for prolonged length of stay in patients with community-acquired pneumonia based on Japanese administrative data, 59 Respiratory Investigation 194-203 (Nov. 8, 2020) (Year: 2020).*
International Application No. PCT/US2023/024005 filed May 31, 2023—International Search Report and Written Opinion issued on Aug. 30, 2023; 18 pages.

* cited by examiner

PATIENT 101

Admission Data 110

ICD & Elixhauser Codes 112

Insurance & Demographics Data 114

Patient Flow Data 116

Surgery & Special Condition Data 118

Labs, Vitals, & Imaging Data 120

PATIENT LOS PREDICTION MODEL 102

PREDICTED LENGTH OF STAY 104

DATE CALCULATOR 106

PREDICTED DISCHARGE DATE 150

METHODS AND SYSTEMS FOR PATIENT DISCHARGE MANAGEMENT

FIELD

Embodiments of the subject matter disclosed herein relate to managing patients of a healthcare facility, and more particularly, to monitoring patient status.

BACKGROUND

A demand for resources of a healthcare facility (e.g., beds, ventilators, etc.) may be high, to provide appropriate care to a continuous stream of patients with serious medical conditions. An important responsibility of care providers working in a healthcare facility is determining when patients may be discharged, to free up resources of the healthcare facility for new patients. An average length of stay for patients with a same condition as the patient (e.g., a geometric mean length of stay, or GMLOS) may be provided, for example, within a patient manager software application. However, the GMLOS may not be accurate, as a result of not taking into consideration specific health issues of the patient. An expected discharge date (EDD) of a patient may also be provided in the patient manager software application by a physician. However, the EDD may not be accurate due to an amount of the physician's time needed to determine an accurate EDD. Reviewing patient records in an EHR system to determine whether a patient may be ready to discharge may be laborious and time consuming. The patient data to be reviewed may include numerous medical procedures and records generated during investigations of the patient, including a variety of examinations such as blood tests, urine tests, pathology reports, image-based scans, etc. The data may be stored in an Electronic Health Record (EHR) system, which may aggregate information from a plurality of different computer systems and databases. Sorting and extracting information may be a slow and inefficient process, increasing a likelihood of missing records with relevant data which may be spread out across a large number of less informative records.

As a result, an accurate determination of when a patient may be discharged may not be made with sufficient advance notice to efficiently manage patient discharges. The patient discharges may be delayed due to preparations such as filing paperwork, arranging transportation, and other administrative tasks not being performed in a timely manner. Delayed patient discharges may reduce an efficiency in resource allocation within the healthcare facility.

BRIEF DESCRIPTION

In one embodiment, a method for a patient management system of a healthcare facility comprises receiving a selected confidence level from a user of the patient management system; predicting a date for discharging a patient of the healthcare facility using a trained length of stay (LOS) prediction model, based on a set of patient data of the patient, the LOS prediction model trained on historical patient data of the healthcare facility; predicting a discharge date window of the patient, based on the received confidence level; generating a predicted discharge date window element summarizing the predicted discharge date window in a user interface (UI) of the patient management system; and displaying the UI on a display device of the patient management system.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
FIG. 1 is a first data flow diagram showing an exemplary patient discharge date prediction system, in accordance with an aspect of the disclosure.

The following description relates to systems and methods for managing patients in a hospital or healthcare organization. Efficient patient management may include predicting when patients will be discharged. By accurately predicting patient discharge dates, care providers may efficiently allocate resources (e.g., beds, ventilators, etc.) in preparation for new patients with serious conditions.

Patient data may be stored in one or more electronic health record (EHR) systems. Different types of patient data may be stored in different locations, accessed via different interfaces, and used in different ways to make decisions about patient care. The medical data may include diagnostic data, pathology data, consultation data, and treatment data, which may be accessed in different ways. In some examples, a care provider may consult diagnostic data by accessing a first system, pathology data by accessing a second system, consultation data by accessing a third system, and treatment data by accessing a fourth system. In other examples, the diagnostic data, pathology data, consult data, and treatment data may be accessible via a single EHR system, but a user may have to perform a different set of actions (e.g., entering in search terms, selecting controls, etc.) from different reference points to view each different type of data. Viewing and considering such data independently when making patient care decisions may lead to overlooked information that may affect a treatment decision, and may increase time burden and mental load placed on the clinicians caring for a patient.

As disclosed herein, the issues described above may be addressed by an AI-based, computerized patient discharge date prediction system that automatically retrieves and aggregates data relevant to health conditions of a plurality of patients, and generates predicted discharge dates for the plurality of patients. The predicted discharge dates may be used to generate predicted date windows for discharging patients, at varying levels of confidence. For example, a first discharge date window may be a first range of dates during which a patient has an estimated 90% chance of being discharged within the first discharge date window. A second discharge date window may be a second range of dates during which a patient has an estimated 60% chance of being discharged within the second discharge date window. As a result of having a lower confidence level (e.g., 60% vs 90%), the second range of dates of the second discharge date window may be a narrower range of dates than the first range of dates of the first discharge date window.

The automatic generation and display of patient predicted discharge date windows (also referred to herein as discharge window predictions) may reduce an amount of time spent by a care provider in determining statuses of a rotating body of patients, thereby increasing an amount of time available to the care provider to attend to patients. Further, a cognitive load placed on the care provider may also be reduced, thereby reducing a probability of error in assessing when a patient may be discharged.

Embodiments of the present disclosure will now be described, by way of example, with reference to the figures. FIG. 1 shows a flow of data through an exemplary patient discharge date prediction system, such as the patient discharge date prediction system of FIG. 2. The patient discharge date prediction system may generate a graphical element indicating a predicted discharge date, or discharge date window, in a user interface (UI) of a patient manager web application, such as the UI of FIG. 3. The patient data used to predict the discharge date may be generated over a patient timeline, as shown in FIG. 4. Prior to being processed, the patient data may be organized and/or structured based on a stacked approach of FIG. 5A, from which a data vector comprising encoded patient data may be created, as shown in FIG. 5B. The data vectors of encoded patient data may be used to train a patient length of stay (LOS) prediction model, based on the LOS prediction model training system shown in FIG. 6A. The LOS prediction model may be trained by following one or more steps of the method shown in FIG. 8. FIG. 6B shows the patient LOS prediction model in use during deployment, where the LOS prediction model may generate a predicted length of stay of a patient by following one or more steps of the method shown in FIG. 7. The patient discharge date prediction system may then convert the length of stay prediction to a predicted date of discharge, or discharge date window, which may be displayed in the UI.

Referring now to FIG. 1, a flow of data through an exemplary patient discharge date prediction system 100 of a hospital network is shown. Patient discharge date prediction system 100 includes a patient LOS prediction model 102, which may predict an amount of time a patient 101 is expected to stay (e.g., length of stay) in one or more hospitals of the hospital network. The expected stay of patient 101 may be predicted from a plurality of patient data of patient 101, which may be received from a plurality of EHR's and/or databases of the hospital network.

For example, patient discharge date prediction system 100 may receive one or more secure feeds of patient data, where as a result of the patient data being included within the hospital network, a security of the data may be established whereby the patient data may be received without using encryption and/or authentication. In various embodiments, the secure feeds may be generated by patient discharge date prediction system 100, where patient discharge date prediction system 100 may automatically and/or regularly request patient data from the plurality of EHR's and/or databases of the hospital network. For example, patient discharge date prediction system 100 may request a first set of data from a first EHR of the hospital network, and receive a first secure feed from the first EHR including the first set of data; patient discharge date prediction system 100 may request a second set of data from a second EHR of the hospital network, and receive a second secure feed from the second EHR including the second set of data; and so on.

The one or more secure feeds may include patient data of various types. For example, the patient data received in the one or more secure feeds may include admission data 110 of patient 101. Admission data 110 may include information pertaining to an admission of patient 101 into a hospital of the hospital network, such as a date and time of admission, a health condition and/or symptoms for which patient 101 was admitted, a primary care provider of patient 101, contact information of patient 101, and the like. The patient data may include International Classification of Diseases (ICD) and Elixhauser Comorbidity Index codes 112, which may indicate a disease or health condition of patient 101. The patient data may include insurance and demographics data 114. The patient data may include patient flow data 116, which may indicate a trajectory of patient 101 through a healthcare system such as the healthcare system offered by the hospital network. For example, the trajectory may include prior diagnoses, treatments, and stays at one or more hospitals of the hospital network. The patient data may include surgery and special condition data 118, which may indicate one or more surgeries performed on patient 101, as well as outcomes of the surgeries and any discoveries made during the surgeries. The patient data may include labs, vital sign data, and imaging data 120, which may include results from tests, studies, and/or panels performed on patient 101, data received at one or more EHRs of the hospital network from patient monitors arranged at or on patient 101, and/or results of computed tomography (CAT), magnetic resonance (MR), and/or other imaging studies performed on patient 101. It should be appreciated that the examples provided herein are for illustrative purposes, and other types of patient data may be included in one or more secure feeds without departing from the scope of this disclosure.

Patient LOS prediction model 102 may receive the patient data from patient 101 as input, and may output a predicted LOS 104. For example, the predicted LOS 104 may be a number of days that patient 101 is expected to remain a patient of a hospital of the hospital network, based on historical patient data used to train the patient LOS prediction model 102. Predicted LOS 104 may be an input into a date calculator 106 of the patient discharge date prediction system 100, which may calculate a predicted discharge date 150 of patient 101 based on predicted LOS 104 and a current date.

Thus, according to embodiments disclosed herein, a patient discharge date prediction system may be employed to retrieve and compile relevant patient status information from a variety of sources, and automatically generate and display discharge date predictions for patients at a hospital. The discharge date predictions may facilitate an efficient and timely preparation for discharging patients from the hospital. The generation and display of the discharge date predictions may reduce a footprint of the patient medical data and may reduce the cognitive load on the user/clinician.

Figure 2:
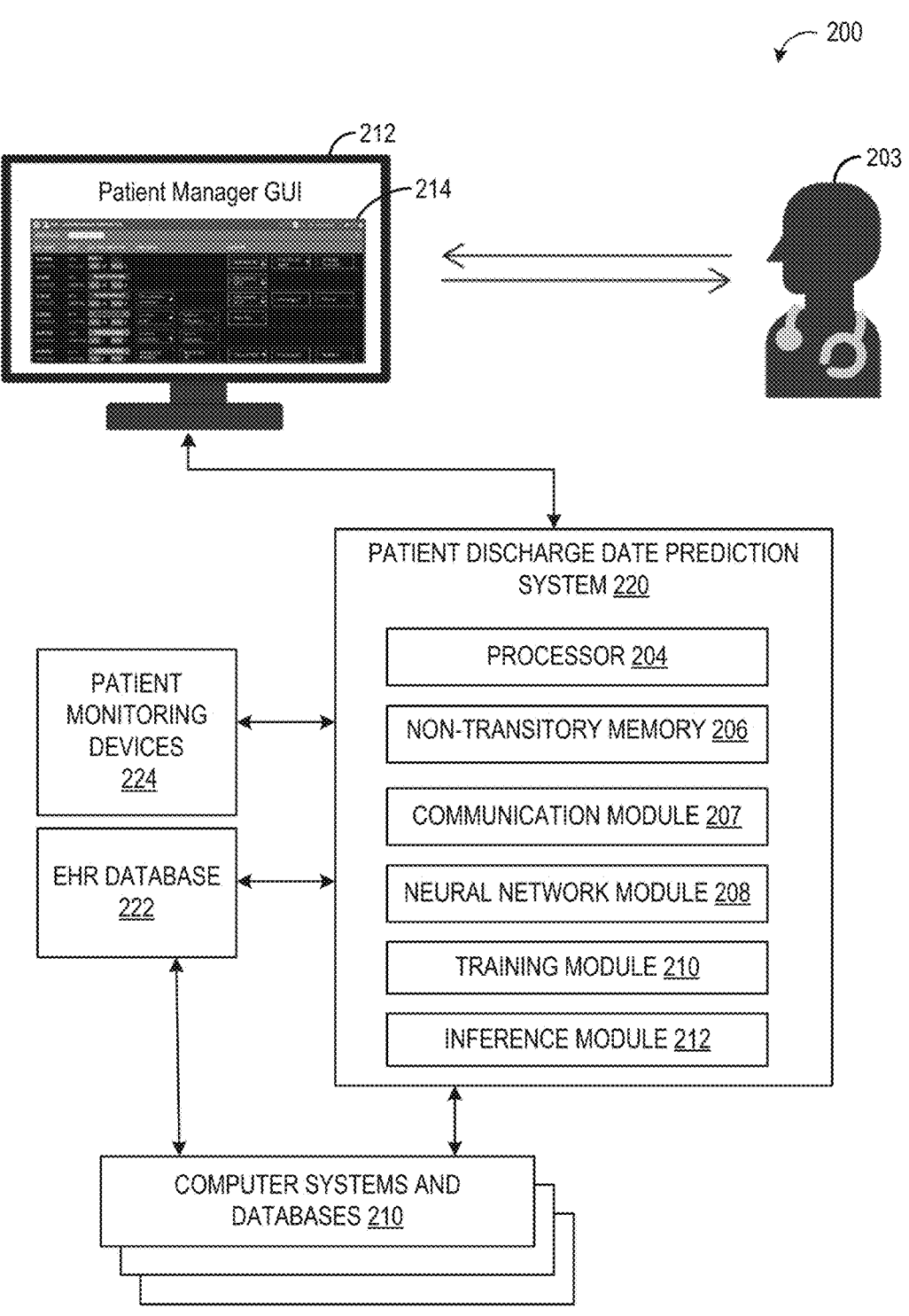
FIG. 2 is a schematic block diagram showing components of an exemplary patient discharge date prediction system, in accordance with an aspect of the disclosure.

FIG. 2 shows a patient management system 200 according to an aspect of the disclosure. Patient management system 200 may include a patient discharge date prediction system 220 configured for predicting a discharge date window of a patient that may be displayed, along with associated clinical information, to a user 203 via a display 201. Display 201 may be any known device having a screen to display the discharge window prediction and the clinical information. The clinical information may be stored in and/or may be retrieved from one or more computer systems or databases 230 of patient management system 200. The clinical information may be generated during investigations of the patient (e.g., clinical visits, examinations, tests) and may include a variety of medical records including examination reports, blood tests, urine tests, pathology reports, and scans using various medical imaging systems such as ultrasound, magnetic resonance imaging, computed tomography systems, and other radiological investigations. These medical records generated from various investigations may be stored in different formats. For example, the medical images may be stored in a digital imaging in medical communication (DICOM) format, which is different from a format for storing the blood parameter reports, which is different from the format of storing the pathological reports, and so on.

Display device 201, and in some examples, more than one display device, may be communicatively coupled to patient discharge date prediction system 220. Display device 201 may include a processor, memory, communication module, user input device, display (e.g., screen or monitor), and/or other subsystems and may be in the form of a desktop computing device, a laptop computing device, a tablet, a smart phone, or other device. Display device 201 may be adapted to send and receive encrypted data and display medical information, including medical images in a suitable format such as digital imaging and communications in medicine (DICOM) or other standards. Display device 201 may be located locally at a medical facility, or the display device may be a mobile device accessed remotely from the medical facility (such as a care provider's mobile phone).

The patient discharge window predictions may be viewed via a user interface (UI) 214 (which may be a graphical user interface or GUI) of display device 201. When viewing the patient discharge window predictions via UI 214, a care provider may enter input (e.g., via a user input device, which may include a keyboard, mouse, microphone, touch screen, stylus, or other device) that may be processed by patient discharge date prediction system 220. In examples where the user input is a selection of a link or control button of UI 214, the user input may trigger display of additional clinical information relevant to one or more patients, or other actions.

Patient management system 200 may include an electronic health record (EHR) database 222, which may be communicatively coupled to patient discharge date prediction system 220. EHR database 222 may be stored in a mass storage device configured to communicate with secure channels (e.g., HTTPS and TLS), and store data in an encrypted format. Further, EHR database 222 may be configured to control access to patient electronic medical records such that only authorized healthcare providers may edit and access the electronic health records. An EHR for a patient may include medical device data (e.g., vital signs measured or otherwise ascertained by medical devices such as heart rate, oxygen saturation, etc.), user-specified medical parameters (e.g., acuity scores, pain scores), patient demographic information, family medical history, past medical history, lifestyle information, preexisting medical conditions, current medications, allergies, surgical history, past medical screenings and procedures, past hospitalizations and visits, and/or other information.

In addition to EHR database 222, the patient information used to generate the discharge window predictions may also be stored in one or more computer systems and databases 230 in communication with patient discharge date prediction system 220 and/or EHR database 222. For example, computer systems and databases 230 may include a picture archiving and communication system (PACS) that may store and communicate medical images and associated reports (e.g., clinician findings), such as ultrasound images, MRI images, etc., in the DICOM format. Computer systems and databases 230 may include a radiology information system (RIS), which may store radiology images and associated reports, such as CT images, X-ray images, etc. Computer systems and databases 230 may include a pathology database, which may store pathology images and related reports, including visible light or fluorescence images of tissue, such as immunohistochemistry (IHC) images. In some embodiments, the patient information used to generate the discharge window predictions may also be received from one or more patient monitoring devices 224 communicably coupled to patient discharge date prediction system 220. It should be appreciated that the example computer systems and databases provided herein are for illustrative purposes, and in various embodiments, additional, fewer, or different computer systems and/or databases may be included without departing from the scope of this disclosure.

Patient discharge date prediction system 220 may include one or more processors 204 and a non-transitory memory 206 to store and execute the methods disclosed herein to generate the discharge window predictions and patient status data, as well as send and receive communications, graphical user interfaces, medical data, and other information. Non-transitory memory 206 may include one or more data storage structures, such as optical memory devices, magnetic memory devices, or solid-state memory devices, for storing programs and routines executed by processor(s) 204 to carry out various functionalities disclosed herein. Non-transitory memory 206 may include any desired type of volatile and/or non-volatile memory such as, for example, static random access memory (SRAM), dynamic random access memory (DRAM), flash memory, read-only memory (ROM), etc. Processor(s) 204 may be any suitable processor, processing unit, or microprocessor, for example. Processor(s) 204 may be a multi-processor system, and, thus, may include one or more additional processors that are identical or similar to each other and that are communicatively coupled via an interconnection bus. Processor(s) 204 may be single core or multi-core, and the programs executed thereon may be configured for parallel or distributed processing. In some embodiments, processor 204 may optionally include individual components that are distributed throughout two or more devices, which may be remotely located and/or configured for coordinated processing. In some embodiments, one or more aspects of processors 204 may be virtualized and executed by remotely-accessible networked computing devices configured in a cloud computing configuration.

In some examples, patient discharge date prediction system 220 may be implemented over a cloud or other computer network. For example, patient discharge date prediction system 220 is shown in FIG. 2 as constituting a single entity, but it should be appreciated that patient discharge date prediction system 220 may be distributed across multiple devices, such as across multiple servers.

Patient discharge date prediction system 220 may be configured to generate and output one or more patient discharge window predictions for display via display 201. Each patient discharge window prediction may include additional clinical information, which may be automatically extracted from the EHRs and/or other medical information of the patient (e.g., pathology reports, imaging scans/reports, etc.) that may or may not be stored as EHRs. In some embodiments, a portion of the extracted clinical information may be assembled into a natural-language-like format and displayed along with and/or adjacent to a relevant discharge window prediction, as described in greater detail below in reference to FIG. 3. For example, the extracted clinical information may include doctor's notes, radiologist notes to assess a condition of a patient, and/or other factors to use as features in machine/deep learning.

As used herein, the term "module" may include a hardware and/or software system that operates to perform one or more functions. For example, a module may include a computer processor, controller, or other logic-based device that performs operations based on instructions stored on a tangible and non-transitory computer readable storage medium, such as a computer memory. The device may be an off-the-shelf device that is appropriately programmed or instructed to perform operations described herein from the instructions described above. Alternatively, a module may include a hard-wired device that performs operations based on hard-wired logic of the device. Various modules shown in the attached figures may represent the hardware that operates based on software or hardwired instructions, the software that directs hardware to perform the operations, or a combination thereof.

Patient discharge date prediction system 220 may include a communication module 207. Communication module 207 may facilitate transmission of electronic data within and/or among one or more systems. Communication via communication module 207 may be implemented using one or more protocols. In some examples, communication via communication module 207 occurs according to one or more standards (e.g., Digital Imaging and Communications in Medicine (DICOM), Health Level Seven (HL7), ANSI X12N, etc.). Communication module 207 can be a wired interface (e.g., a data bus, a Universal Serial Bus (USB) connection, etc.) and/or a wireless interface (e.g., radio frequency, infrared, near field communication (NFC), etc.). For example, communication module 207 may communicate via wired local area network (LAN), wireless LAN, wide area network (WAN), etc. using any past, present, or future communication protocol (e.g., BLUETOOTH™, USB 2.0, USB 3.0, etc.).

Patient discharge date prediction system 220 may include a neural network module 208. Neural network module 208 may store one or more patient discharge window prediction models that may be used to generate the discharge window predictions. The patient discharge window prediction models may include one or more machine learning (ML) models and/or deep learning models (e.g., neural networks), and instructions for implementing the one or more patient discharge window prediction models to predict a patient discharge window, as described in greater detail below. Neural network module 208 may include trained and/or untrained neural networks and may further include various data, or metadata pertaining to the one or more neural networks stored therein.

Patient discharge date prediction system 220 may include a training module 210, which may comprise instructions for training one or more of the neural networks stored in neural network module 208. Training module 210 may include instructions that, when executed by processor(s) 204, cause patient discharge date prediction system 220 to conduct one or more of the steps of a method for generating a training data set and training a patient LOS prediction model (e.g., the LOS prediction model 102 of FIG. 1), as described in more detail below in reference to FIG. 8. In some embodiments, training module 210 may include instructions for implementing one or more gradient descent algorithms, applying one or more loss functions, and/or training routines, for use in adjusting parameters of one or more neural networks of neural network module 208. Training module 210 may include training datasets for the one or more neural networks of neural network module 208.

Patient discharge date prediction system 220 may include an inference module 212. Inference module 212 may include instructions for deploying a trained patient discharge window prediction model, for example, to predict a discharge window of a patient, as described in FIG. 7. In particular, inference module 212 may include instructions that, when executed by processor 204, cause patient discharge date prediction system 220 to conduct one or more of the steps of the method 700, as described in further detail below.

Thus, patient discharge date prediction system 220 may generate predictions of when patients of a healthcare facility may be discharged. In some embodiments, patient discharge date prediction system 220 may generate predictions periodically or regularly at scheduled times. For example, patient discharge date prediction system 220 may generate predictions at several scheduled times during a day. In other embodiments, Patient discharge date prediction system 220 may generate predictions based on an availability of new patient data. For example, if no new patient data is available, patient discharge date prediction system 220 may not generate the predictions, and in response to new patient data becoming available, patient discharge date prediction system 220 may generate (and display) the predictions. In this way, patient discharge date prediction system 220 may perform the task of retrieving patient data relating to the discharge window predictions from EHR database 222 and computer systems and databases 230, and analyzing the retrieved data for the care provider, thereby advantageously reducing an amount of time spent by the care provider finding and analyzing data to determine when a patient may be discharged. Further, the information may be retrieved in background processing to increase computational efficiency.

While not specifically shown in FIG. 2, additional devices described herein (e.g., display device 201) may likewise include user input devices, memory, processors, and communication modules/interfaces similar to communication module 207, non-transitory memory 206, and processor(s) 204 described above, and thus the description of communication module 207, non-transitory memory 206, and processor(s) 204 likewise applies to the other devices described herein. As an example, display device 201 may store user interface templates in memory that include placeholders for relevant information stored on patient discharge date prediction system 220 or received via patient discharge date prediction system 220, which a user of display device 201 may configure. The discharge window predictions and relevant patient information may be retrieved from patient discharge date prediction system 220 and inserted in the placeholders. The user input devices may include keyboards, mice, touch screens, microphones, or other suitable devices.

Figure 3:
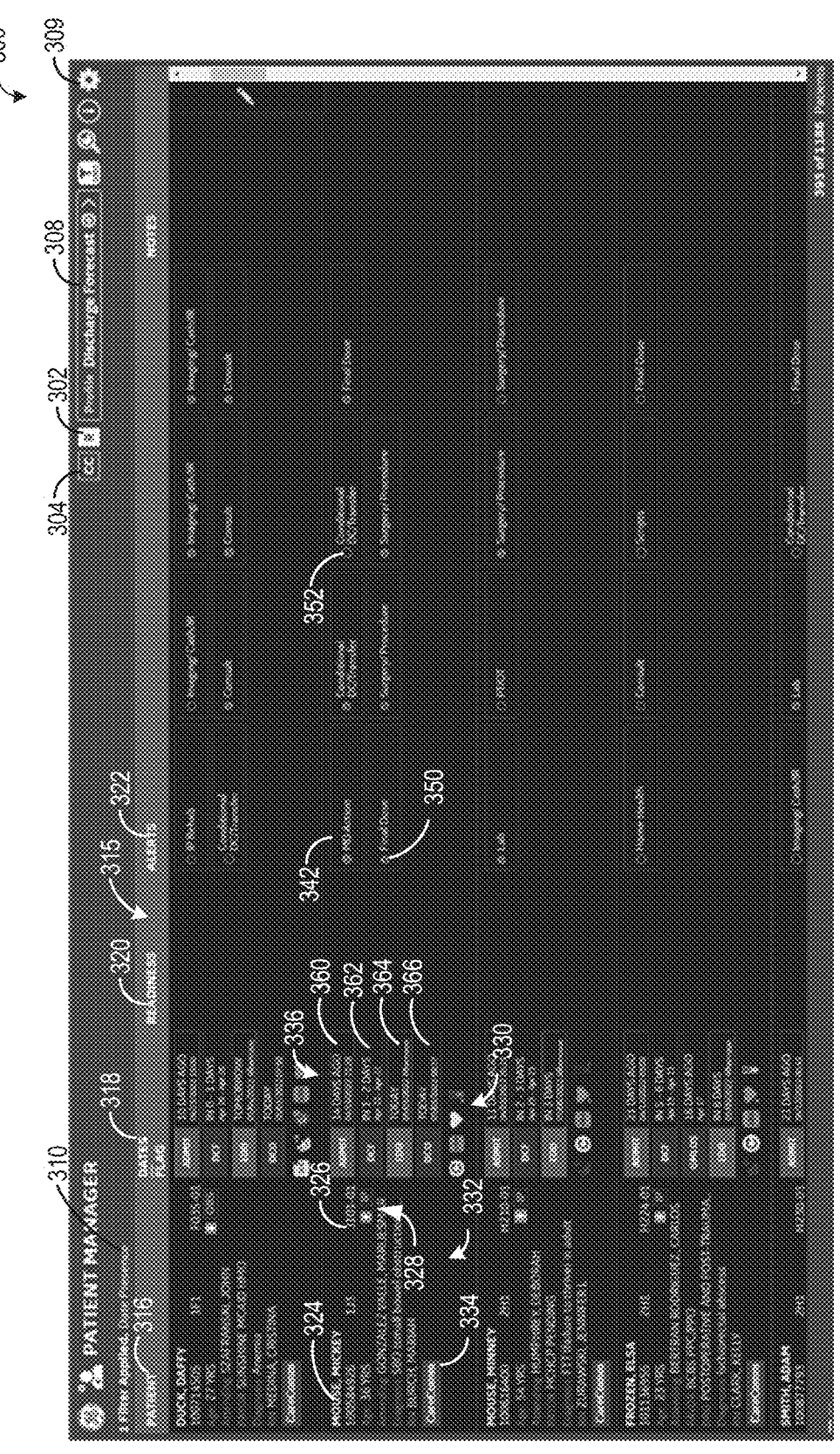
FIG. 3 shows an example user interface of a patient management system including the patient discharge date prediction system of FIG. 2, in accordance with an aspect of the disclosure.
Figure 4:
FIG. 4 shows a timeline along which patient data may be generated, in accordance with an aspect of the disclosure.
Figure 4:
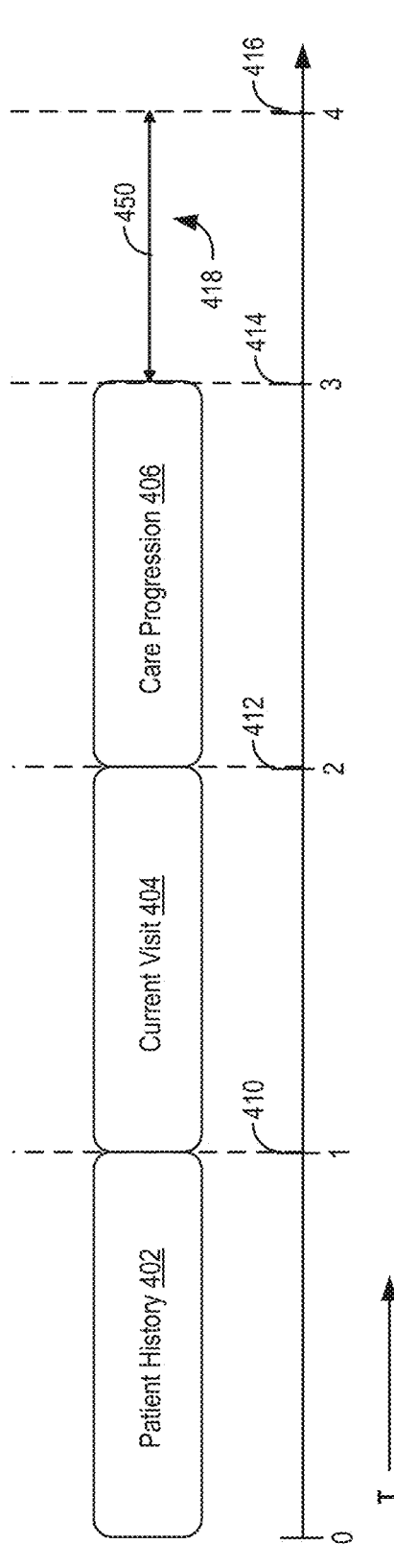

Turning to FIG. 3, an embodiment of a graphical UI 300 is shown of a patient management application including a patient discharge date prediction system. The patient management application may be a non-limiting embodiment of patient management system 200 of FIG. 2. UI 300 may be a non-limiting example of UI 214 of patient discharge date prediction system 220 of FIG. 2. UI 300 may be displayed on a display device (e.g., display device 201) of the patient management application during operation in a healthcare facility. Specifically, UI 300 may be displayed to a care provider of the healthcare facility when the care provider uses the patient discharge date prediction system to generate discharge window predictions for patients of the healthcare facility, as described in greater detail below in reference to FIGS. 4-8. The discharge window predictions may be used to determine when one or more patients may be discharged and/or to assess an availability of resources (e.g., beds) of the healthcare facility. UI 300 may include a plurality of different individual discharge window predictions for a respective plurality of patients, which may be displayed in rows of UI 300.

UI 300 may be displayed in different alternative views. In some embodiments, UI 300 may be displayed either in a rounding (e.g., enhanced) view, where information is displayed in a fixed format that is not customizable by the user, or in a condensed or command center view, where less information is displayed in a variable format that is customizable by the user. The user may customize the condensed view by hiding one or more columns, rows, sections, or elements of the enhanced view. For example, a first user may view UI 300 in a first condensed view that is customized to hide a first portion of patient data displayed in UI 300, in order to view more rows (e.g., patients) in a single screen. A second user may view UI 300 in a second condensed view that is customized to hide a column of UI 300, in order to more easily view data displayed in a different column. A third user may view UI 300 in a third, enhanced view, in order to view a comprehensive set of data. Each of the first user, the second user, and the third user may select a desired view and/or switch between desired views by selecting one or more controls of UI 300, such as a rounding view toggle switch 302 or a command center view toggle switch 304.

In some embodiments, when UI 300 is displayed, a display panel 315 may automatically generate and show discharge window predictions for patients of a selected medical facility. In other embodiments, display panel 315 may not automatically generate and show the discharge window predictions, and the user may initiate display of the discharge window predictions by selecting a different control element, such as a discharge forecast button 308.

In some embodiments, one or more filters may be applied to UI 300 to filter patient data shown in UI 300. The one or more filters may be selected, for example, via controls accessible via a settings button 309. A summary of one or more filters applied may be displayed in filter bar 310.

As one example, in response to a situation where numerous patients are afflicted with a particular condition, a physician may wish to view discharge window predictions for patients across all hospital units who suffer from the particular condition, in order to determine how many patients may be eligible to discharge free up beds at the hospital units. Using the one or more filters, the user may enter in the particular condition, and select a "display discharge window predictions" button to view the discharge window predictions.

In the embodiment shown in FIG. 3, the discharge window predictions may be displayed in rows of UI 300, where each row corresponds to a patient of the selected hospital unit. The discharge window predictions and other information may be displayed in columns of UI 300. In other embodiments, a layout of the information may be different. For example, in other embodiments, each patient of the selected hospital unit may be displayed in a separate column, and the discharge window predictions and other information may be displayed in rows of UI 300. It should be appreciated that the layout and juxtaposition of the elements of UI 300 may vary in different embodiments, and the elements may appear in different visual configurations without departing from the scope of this disclosure. Additionally, not all of the elements shown in UI 300 may be included in an embodiment, and some embodiments may include a greater or lesser number of elements.

Further, the elements of UI 300 may be controls (e.g., buttons) that may be selected by a user via a user input device (e.g., a mouse, a touchscreen, etc.). When the user selects the a visual element, additional information relevant to the element may be displayed, for example, in a pop-up display panel or on a different screen of UI 300. Further, in some examples, different information may be displayed when the user enters different user input. In such examples, a first pop-up display panel may be displayed when the user selects the element with a first type of user input, such as a hover (e.g., where the user positions a cursor or other user input locator over the element but does not enter further user input). A second pop-up display panel may be displayed when the user selects the element with a second type of user input, such as selecting the element with one or more clicks or touches.

UI 300 may include a patient info column 316, which may show identifying and general information of a patient. For each row of UI 300, a patient data panel 332 that includes patient information may be displayed for a corresponding patient in the patient info column 316. Patient data panel 332 may include a patient name (or abbreviated name) 324. A location code 326 may also be included in the patient data panel 332, which may indicate a current location of the patient in the hospital or hospital system (e.g., the ICU to which the patient has been assigned and/or is currently registered). One of more patient location icons 328 may also be displayed, which may indicate, for example, patient location information such as a current unit in which the patient is being taken care of, as well as historical predictions along a past patient pathway. Patient data panel 332 may also include other general information, such as, for example, an identification number of the patient, an age and/or date of birth of the patient, an attending physician or nurse of the patient, patient insurance information, a diagnosis of the patient, and the like. Further, some aspects of patient information may be visualized via one or more icons 330.

In some embodiments, a care communication button 334 may be included in patient data panel 332, which when selected may generate an alert that may be sent to other care providers and/or saved as part of the patient's EHR to indicate that an ordered or commanded patient task has yet to be initiated or completed. However, in some examples, care communication button 334 may be omitted or may trigger other types of communication or alerts.

UI 300 may include a dates column 318, where dates column 318 includes a dates panel 336 for each patient displayed. Dates panel 336 may show a timeline of events relating to changes in a status of each patient during a time spent by the patient at the healthcare facility, including dates and times of the events. In some embodiments, the timeline may begin at a time of admission of a patient, which may be indicated via an admit graphical element 360. Dates panel 336 may also include an expected discharge date (EDD) element 364, which may indicate a projected discharge data based on historical data collected from a plurality of patients with a same health condition as the patient. In other embodiments, a mean length of stay for patients with the same condition as the patient (e.g., a geometric mean length of stay, GMLOS) may be included. Additionally, as described in greater detail below, the patient discharge date prediction system may predict a discharge date 366 for one or more patients based on an output of a patient discharge date prediction model. In various embodiments, dates panel 336 may include a predicted discharge date window element 362, where the predicted discharge date window is based on the predicted discharge date. For example, the predicted discharge date window may be a date range including the predicted discharge date. Additionally or alternatively, the predicted discharge date window may be expressed relative to a current day, such as "In 1-2 days", "In 1 week", or similar description.

Additionally, a length of the discharge window (e.g., a number of days of the date range) may be based on a desired confidence level, where the desired confidence level reflects a level of confidence that the patient may be discharged within the discharge window. For example, if the desired confidence level is high (e.g., 80%), the length of the discharge window may be extended to include a wider range of dates, to achieve the desired level of confidence that the patient may be discharged within the discharge window. Alternatively, if the desired confidence level is lower (e.g., 50%), the length of the discharge window may be reduced to include a narrower range of dates. If the desired confidence level is very low (e.g., 10%), the predicted discharge date window may be the predicted discharge date.

In various embodiments, the desired confidence level may be configured in the patient discharge date prediction system by a user, or an administrator of the healthcare facility. For example, in some embodiments, the user may select the desired confidence level via a menu of UI 300, such as by selecting a setting from a menu displayed as a result of the user selecting the settings button 309. In other embodiments, the administrator may pre-configure to desired confidence level based on administrative guidelines of the healthcare facility. The confidence level may be displayed in or next to the predicted discharge date window element 362, so that the user may see the confidence level used to generate the discharge window prediction from the predicted discharge date.

UI 300 may include an alerts column 322, which may show one or more patient alerts. The one or more alert elements 342 may be included in a row of UI 300 corresponding to a patient. The one or more alert elements 342 may include patient alerts generated by one or more EHR systems or other computer systems of a healthcare organization of which the hospital unit is a part (e.g., EHR database 222 and/or computer systems and databases 230 of FIG. 2). For example, an EHR system may generate a flag for a patient indicating that the patient is overdue for a test or examination, that certain records or paperwork are missing, that a patient is scheduled for a procedure but has lab results to be consulted prior to performing the procedure, or other suitable alert. The one or more alert elements 342 may also include one or more pending discharge milestones, representing tasks to be carried out or completed prior to discharging the patient, pending reports or results, operational logistics involved in transferring the patient, and/or other reminders, warnings, or additional information. In some embodiments, the one or more alert elements 342 may be controls that may be selected. When an alert element 342 is selected, additional information regarding the alert may be displayed via an additional (e.g., pop-up) display panel, or an external system (such as an EHR system) may be launched to allow a user to view the additional information.

In some embodiments, the patient discharge date prediction system may run regularly or periodically, and the predicted patient discharge window and/or patient data may be periodically updated automatically by the patient discharge date prediction system. In other embodiments, the patient discharge date prediction system may be launched by a care provider when the care provider wishes to determine if one or more patients of an ICU may be discharged. For example, a care provider may start the patient discharge date prediction system and view predicted discharge date window elements 362 of a plurality of patients at a first time. At the first time, the care provider may see that no patients are close to a predicted discharge date window. The care provider may leave the patient manager to attend to patients, and return later to the patient manager, to view the predicted discharge date window elements 362 of the plurality of patients at a second time. In between the first time and the second time, elements of patient data and/or discharge window predictions may change, for example, due to more recent data being recorded in one or more EHR systems. As a result of the more recent data being recorded, at the second time, the care provider may see that a patient that was previously not close to a predicted discharge date window is now close to the predicted discharge date window. As a result of seeing that the patient is now close to the predicted discharge date window, the care provider may initiate one or more tasks in preparation for discharging the patient. For example, the tasks may include initiating paperwork, arranging for transportation, preparing to place a new patient, preparing the patient for discharging, and managing resources and tasks such as medical equipment, medication, home care resources, and others depending on a lead time for management. Thus, the patient discharge date prediction system may serve to provide updated data that may aid the care provider in managing patients of the healthcare facility.

In some embodiments, if a current date falls within the predicted discharge date window, the patient discharge date prediction system may generate an alert at the predicted discharge date window element 362 indicating to the care provider that a discharge of a patient may be pending or approaching. For example, a level of illumination of the predicted discharge date window element 362 may be increased, or a color of the predicted discharge date window element 362 may be changed, or a different visual indication of the pending or approaching discharge may be provided. Further, in some embodiments, if the current date falls within the predicted discharge date window, the patient discharge date prediction system may generate one or more notifications to one or more care providers of the patient. For example, a message may be sent to the one or more care providers indicating one or more administrative tasks to be performed prior to discharging the patient, such as paperwork to be filled out, transportation arrangements to be made, family members to be contacted, and the like.

Thus, while patient data relevant to patient discharges is updated asynchronously in one or more systems and/or databases coupled to the patient discharge date prediction system, a predicted discharge date window of a patient based on a most recent version of the patient's data may be displayed in UI 300. In this way, the patient discharge date prediction system may provide an efficient and user-friendly way to monitor patient discharge information via a single interface, without having to repeatedly access various EHR systems to ensure accuracy of the patient data and/or while the various EHR systems are in an unlaunched state (e.g., not consuming computing and/or network resources of the healthcare system). Additionally, in some embodiments, a "last update date/time" may be included in the predicted discharge date window element 362, which may indicate to the user the last time that the discharge window prediction was updated.

As an example of how UI 300 may be used, a care provider may oversee an unit of a hospital with 10 patients, where all beds of the unit are occupied. The care provider may receive a request from an administration of the hospital to admit another patient. In order to determine whether the patient may be admitted to the unit, the care provider may wish to determine whether one of the 10 current patients may be discharged, to make a bed of the unit available.

The care provider may start a software application (e.g., the patient management application) running the patient discharge date prediction system in one of the ways described above, upon which UI 300 may appear on a display device. The care provider may select a scope of the patient date discharge prediction system (e.g., the unit of the hospital). The patient discharge date prediction system may retrieve a list of patients corresponding to the unit from one or more EHRs and/or hospital computer systems and databases, and generate a plurality of discharge window predictions for the patients on the list. When discharge window predictions have been generated by the patient discharge date prediction system for all of the patients on the list of patients, the discharge window predictions may be outputted to UI 300 for display. Predefined visual elements/controls that correspond to the discharge window predictions (e.g., predicted discharge date window element 362) may be selected and inserted into a template of UI 300 along with corresponding patient identifying data. Additionally, patient alert, discharge milestone, and other elements may be generated (based, for example, on one or more algorithms included in the software application) and displayed in relevant patient rows of UI 300.

When UI 300 displays the discharge window predictions generated by the patient discharge date prediction system, the care provider may see that a patient of the 10 patients of the unit has a predicted discharge date window that includes a current date, indicating that a discharge of the patient is predicted to be imminent. In some embodiments, the 10 patients of the unit may be displayed in UI 300 in a descending order according to a proximity of each patient to a predicted discharge date window of the patient. For example, the patient with the predicted discharge date window that includes the current date may be displayed in a first (e.g., top) row of UI 300; a second patient with a predicted discharge date window starting closest to the current date may be displayed in a second row of UI 300; a third patient with a predicted discharge date window next closest to the current date may be displayed in a third row of UI 300; and so on. In other embodiments, the 10 patients may not be displayed in the descending order, and the predicted discharge date window element 362 for the patient with the predicted discharge date window that includes the current date may be highlighted by a change of color, brightness, a border, and/or an icon, whereby the care provider may easily identify the patient as being predicted to be imminently discharged.

In some embodiments, the care provider may select the predicted discharge date window element 362 of the patient predicted to be imminently discharged, to pop up an additional display panel with more information about the predicted discharge date window. In some embodiments, the care provider may review the information, and confirm the predicted discharge date window by selecting a "confirm" button on the additional display panel. When the discharge window prediction is confirmed, the care provider may be prompted to initiate one or more actions related to discharging the patient, and/or automated workflows may be created based on discharge predictions to prepare care providers and initiate messages for managing resources and discharge tasks.

Additionally or alternatively, via UI 300, the care provider may view one or more alerts generated for the patient, and initiate any tasks that may be entailed by a discharge. As the provider completes a task or meets a milestone relevant to the discharge, the provider may dismiss one or more of the one or more alerts, for example, by selecting a control in a pop-up display panel triggered by selecting an alert. Before closing the application, the care provider may review the predicted discharge date windows of other patients on the list to see when the other patients are predicted to be discharged. The care provider may see that a second patient may be ready to be discharged, and the care provider may initiate a discharge process for the second patient. Alternatively, the care provider may determine that the predicted discharge date window for the second patient is not accurate, for example, based on current patient data available to the care provider but not yet updated in the EHR. If the care provider determines that the predicted discharge date window for the second patient is not accurate, the care provider may update the predicted discharge date window. For example, the care provider may upload additional patient information to the EHR that causes the predicted discharge date window to change, whereby the predicted discharge date window element 362 for the second patient may be updated in UI 300. Additionally or alternatively, the care provider may select discharge window element 362 of the second patient, and insert a comment which may be viewed by one or more other care providers or administrators of the hospital.

Once the patient is discharged, the patient discharge date prediction system may receive an updated location of the patient. Once the patient location is updated, the predicted discharge date window element 362 may be removed from UI 300 for the hospital unit.

Referring now to FIG. 4, a patient care timeline 400 is shown, indicating various periods during which data relevant to predicting a discharge date of a patient of a hospital network is collected. Patient care timeline 400 may be divided into three segments: a patient history segment 402, a current visit segment 404, and a care progression segment 406. Patient data from each of the three segments may include different factors taken into consideration by a patient discharge date prediction system, such as the patient discharge date prediction system 220 of FIG. 2.

Patient history segment 402 may include patient data collected from a beginning of the patient's medical history (e.g., where a time T of patient care timeline 400 is 0), and may extend until a time T=1 of the patient's admission, indicated by a dashed line 410. Patient history segment 402 may include patient data from previous hospital visits, prior conditions suffered by the patient, previous diagnoses and treatments performed within the hospital network, or in other hospital networks, and similar historical healthcare information collected on the patient. Patient data collected during patient history segment 402 may include length of stay data relating to the previous hospital visits, which may be used by an LOS prediction model (e.g., LOS prediction model 102 of FIG. 1) to predict a length of stay of the patient during a current visit at a hospital. For example, previous hospital visit data of the patient may indicate that the patient typically recovers quickly, or that the patient often takes longer than usual to recover.

Current visit segment 404 may include patient data collected from a beginning of the patient's current visit (e.g., at the time T=1 indicated by dashed line 410), and may extend until a time T=2, indicated by a dashed line 412. Current visit segment 404 may include patient data collected initially when the patient is admitted to the hospital. For example, current visit segment 404 may include a primary diagnosis for which the patient is admitted. Current visit segment 404 may include a care pathway, indicating an expected trajectory of the patient through various procedures and treatments. Current visit segment 404 may include data on surgical or other procedures performed on the patient during the current hospital visit. Additionally, current visit segment 404 may include descriptive information of the patient that may influence an amount of time that the patient may remain at the hospital. For example, patient data collected during current visit segment 404 may include a body mass index (BMI), where a larger BMI may indicate a longer recovery time that a smaller BMI. The patient data may include a current age of the patient, where an older patient may have a longer recovery time that a younger patient. The patient data may include other, less serious health conditions and/or health conditions unrelated to the primary diagnosis that the patient may be experiencing. For example, the patient data may include a psychological or emotional state of the patient, or a chronic condition that may complicate treatment of a primary condition of the patient.

Care progression segment 406 may include patient data collected on an ongoing basis over the course of the patient's treatment, starting from the time T=2 indicated by dashed line 412, and extending until a time T=3, indicated by a dashed line 414. Time T=3 may represent an earliest time at which the patient may be discharged from the hospital. Care progression segment 406 may include a current diagnosis of the patient and a current location of the patient within the hospital network. Care progression segment 406 may include patient monitoring information, such as vital sign information collected from one or more patient monitors arranged at or on the patient. Care progression segment 406 may include lab data, or other test results carried out on the patient during treatment. Care progression segment 406 may include a duration of care (e.g., how long a patient has been receiving care for a specific condition).

Patient data from patient history segment 402, current visit segment 404, and care progression segment 406 of patient care timeline 400 may be used as input into the LOS prediction model to predict the patient length of stay at the hospital. Based on the predicted LOS, a predicted discharge date 450 may be generated, where predicted discharge date 450 may be a date after time T=3 (e.g., after an estimated end of care progression segment 406). Further, predicted discharge date 450 may be used to generate a predicted discharge date window 418, which in FIG. 4 extends from time T=3 to a time T=4, indicated by a dashed line 416. Predicted discharge date window 418 may be a date range within which a probability of a discharge of the patient may exceed a pre-configured threshold probability. For example, the pre-configured threshold probability may be 80%, where predicted discharge date window 418 may be a range of dates within which a probability of the patient being discharged exceeds 80%. In other words, the pre-configured threshold probability may reflect a level of confidence that predicted discharge date window 418 is 80% accurate. Thus, a long predicted discharge date window 418 may correspond to a high level of confidence, and a short predicted discharge date window 418 may correspond to a low level of confidence.

Figure 5A:
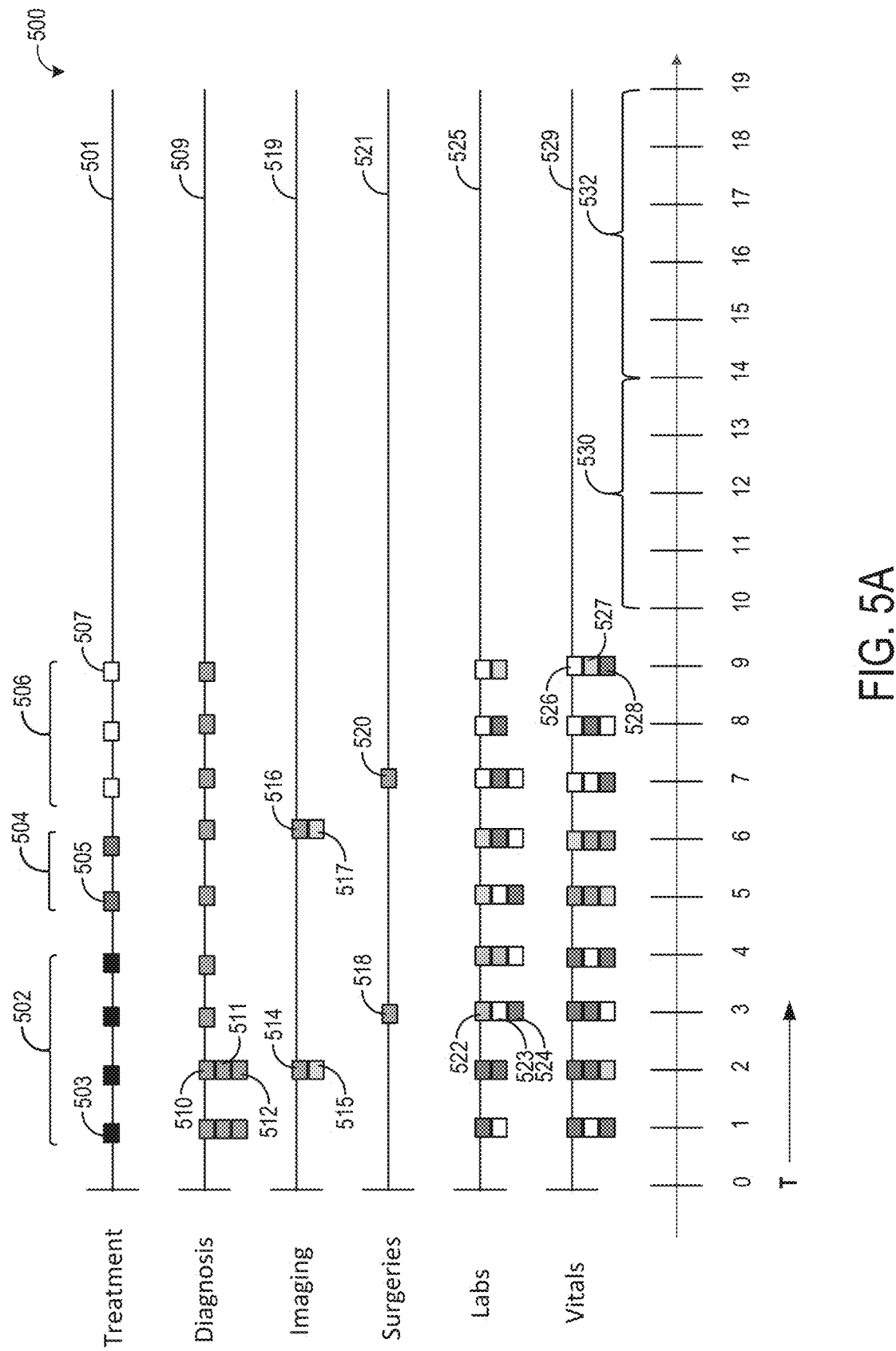
FIG. 5A shows a patient data schematic where different types of patient data are stacked based on a timeline, in accordance with an aspect of the disclosure.
Figure 5B:
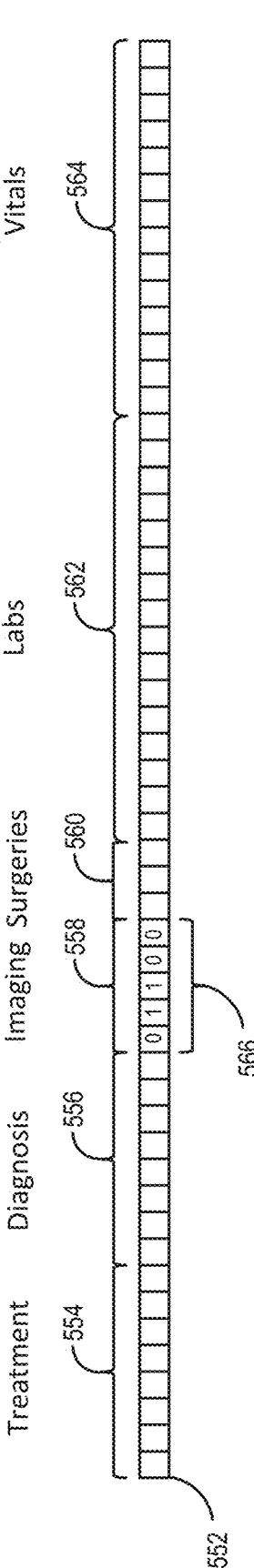
FIG. 5B shows a data vector comprising encoded patient data, in accordance with an aspect of the disclosure.

FIG. 5A shows a patient data schematic 500 where different types of patient data of a patient are stacked in lanes of a timeline, to visually indicate when the different types of patient data are collected. The patient data shown in patient data schematic 500 may be the same as the patient data collected over patient care timeline 400 of FIG. 4. The timeline extends from a time T=0 to a time T=19, where the times T may indicate consecutive dates during the patient's stay at a hospital. For example, a time T=1 may indicate a first day on which the patient was admitted to the hospital; a time T=2 may indicate a second day after the patient was admitted to the hospital; and so on.

Patient data schematic 500 includes six lanes: a treatment lane 501, in which treatment data collected at different times as shown; a diagnosis lane 509, in which diagnosis data collected at different times as shown; an imaging lane 519, in which imaging data collected at different times as shown; a surgeries lane 521, in which surgery data collected at different times as shown; a labs lane 525, in which lab data collected at different times as shown; and a vitals lane 529, in which vital sign data collected at different times as shown. It should be appreciated that the types of data shown in FIG. 5A are for illustrative purposes, and in other embodiments a greater or lesser number of lanes, or different types of patient data, may be included without departing from the scope of this disclosure.

Treatment lane 501 shows a first set of treatments 502 performed on the patient, where the first set of treatments 502 are of a treatment type 503. The first set of treatments 502 includes four treatments, where the four treatments are performed at times T=1, 2, 3, and 4. Treatment lane 501 shows a second set of treatments 504 performed on the patient, where the second set of treatments 504 are of a treatment type 505. The second set of treatments 504 includes two treatments, where the two treatments are performed at times T=5 and 6. Treatment lane 501 shows a third set of treatments 506 performed on the patient, where the third set of treatments 506 are of a treatment type 507. The third set of treatments 507 includes three treatments, where the three treatments are performed at times T=7, 8, and 9.

The patient data depicted in diagnosis lane 509 includes various diagnoses made at different times between a time T=1 and T=9. For example, at a time T=2 (e.g., on a second day at the hospital), three diagnoses were made: a first diagnosis 510, a second diagnosis 511, and a third diagnosis 512. Similarly, patient data schematic 500 shows in imaging lane 519 that a first imaging study 514 and a second imaging study 515 were performed at time T=2, and a third imaging study 516 and a fourth imaging study 517 were performed at time T=6. The patient data depicted in surgery lane 521 includes a first surgery 518 performed at time T=3, and a second surgery 520 performed at time T=7. Patient data schematic 500 shows in lab lane 525 that at time T=3, a first lab result 522 of a first lab test, a second lab result 523 of a second lab test, and a third lab result 524 of a third lab test were recorded. In the vitals lane 529 of patient data schematic 500, it can be seen that at time T=9, readings of a first vital sign 526, a second vital sign 527, and a third vital sign 528 were performed.

The patient data depicted in patient data schematic 500 may be used to predict an LOS of the patient, which in turn may be used to predict a discharge date window within which the patient may be discharged. To predict the LOS of the patient, the patient data included in patient data schematic 500 may be inputted into an LOS prediction model (e.g., the LOS prediction model 102 of FIG. 1), where an output of the LOS prediction model is the predicted LOS of the patient. In various embodiments, the patient data may be inputted into the LOS prediction model as a data vector including an encoding of the patient data, as shown in FIG. 5B.

FIG. 5B shows an exemplary data vector diagram 550, including a data vector 552 comprising encoded patient data, which may be used as input into the LOS prediction model. Data vector 552 may be divided into sections, where each section includes patient data corresponding to a patient data category. In the embodiment shown in FIG. 5B, the patient data categories correspond to the lanes of the timeline depicted in patient data schematic 500 of FIG. 5A. Thus, a first section 554 may correspond to patient data of treatment lane 501. A second section 556 may correspond to patient data of diagnosis lane 509. A third section 558 may correspond to patient data of imaging lane 519. A fourth section 560 may correspond to patient data of surgeries lane 521. A fifth section 562 may correspond to patient data of labs lane 525. A sixth section 564 may correspond to patient data of vitals lane 529. In other embodiments, the patient data categories may correspond to different types of patient data, where there may be a greater or lesser number of different types of patient data than the patient data categories shown in FIG. 5B. In different embodiments, the patient data may be categorized differently. For example, the patient data may be first classified into clinical and nonclinical data, and the clinical data and nonclinical data may both be further subcategorized.

Each section of data vector 552 may include a plurality of consecutive values 566, where the plurality of consecutive values 566 represent an encoding of patient data included in the patient data category corresponding to the section. A number of the plurality of consecutive values 566 may be based on an amount of patient data of the corresponding patient data category. For example, third section 558 may include less consecutive values 566 than fifth section 562, as a result the amount of surgery data of the patient being less than an amount of lab data of the patient.

The plurality of consecutive values 566 included in each section of data vector 552 may be encoded using various different encodings. For example, the consecutive values 566 may include binary values, where the patient data is encoded as a plurality of 0s and 1s, as shown in the third section 558 corresponding to imaging data (e.g., the imaging data of imaging lane 519). In other words, the binary string "0 1 1 0 0" may represent first imaging study 514 and second imaging study 515 performed at time T=2, and third imaging study 516 and a fourth imaging study 517 performed at time T=6, of FIG. 5A. In other embodiments, different types of encodings may be used. For example, a unique number may be assigned to each data point of a patient data category, and data vector 552 may comprise a set of all numbers corresponding to patient data of the patient.

In various embodiments, the LOS prediction model may be a neural network model, such as a convolutional neural network (CNN), and data vector 552 may be inputted into an input layer of the CNN.

Figure 6A:
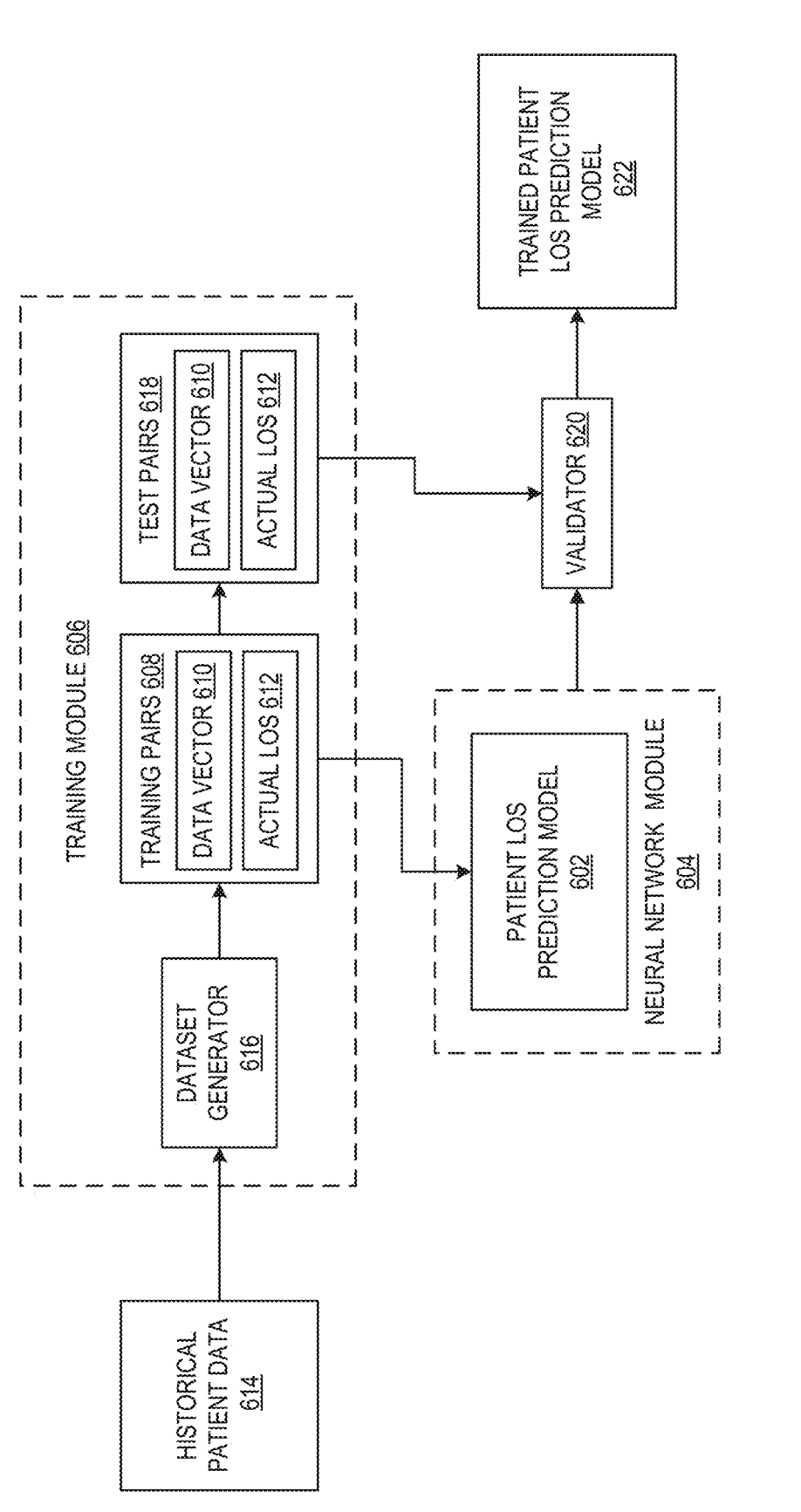
FIG. 6A shows a block diagram of an exemplary embodiment of a patient length of stay (LOS) prediction model training system, in accordance with an aspect of the disclosure.
Figure 6B:
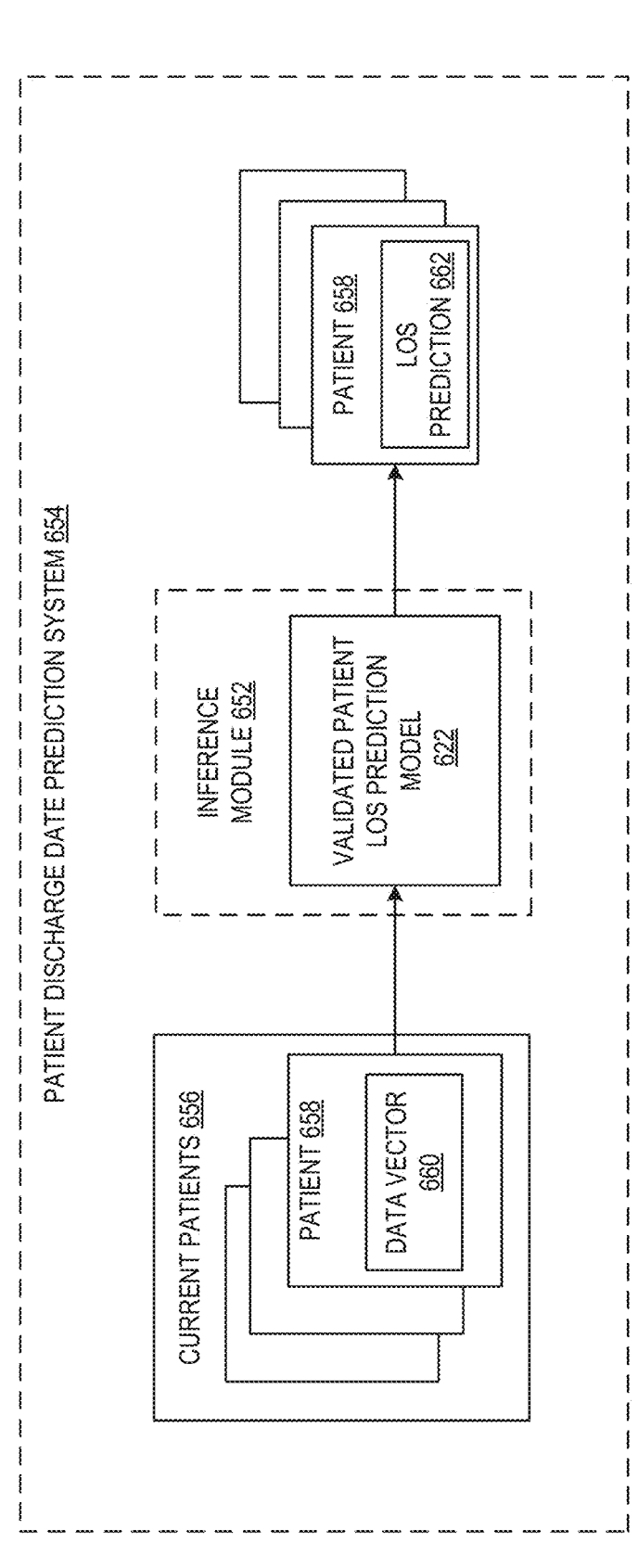
FIG. 6B shows a block diagram of a patient LOS prediction model in use during deployment, in accordance with an aspect of the disclosure.

Referring now to FIG. 6A, an example of an LOS prediction model training system 600 is shown, where the LOS prediction model is a neural network model including a CNN. LOS prediction model training system 600 may be implemented by a patient discharge date prediction system, such as patient discharge date prediction system 100 of FIG. 1, to train the CNN to predict a length of stay of a patient based on patient data of the patient. In an embodiment, LOS prediction model training system 600 includes a patient LOS prediction model 602, to be trained, which may be part of a neural network module 604 of the patient discharge date prediction system (e.g., neural network module 208 of FIG. 2).

The patient LOS prediction model may be trained on a training dataset, which may be stored in a training module 606 (e.g., training module 210 of FIG. 2). The training dataset may comprise a plurality of training pairs 608. Each training pair 608 may include input data, and ground truth target data.

In an embodiment, the input data of each training pair 608 may be a data vector 610, where data vector 610 is a vector of values encoding patient data of a historical patient (e.g., data vector 552 of FIG. 5B). The ground truth target data may be an actual LOS 612 of the historical patient, which may be the length of stay of the patient corresponding to data vector 610. Data vector 610 and actual LOS 612 of training pair 608 may be obtained from historical patient data 614. Historical patient data 614 may be archived and de-identified patient data stored, for example, in one or more databases of a hospital network (e.g., computer systems and databases 230 of FIG. 2).

In various embodiments, data vector 610 and actual LOS 612 may be generated from historical patient data 614 by a dataset generator 616. In one embodiment, dataset generator 616 may organize and/or structure historical patient data 614 in the stacked, timeline approach as depicted in patient data schematic 500 of FIG. 5A, to generate data vector 610 in the manner described in reference to FIG. 5B. The data may be stacked based on data categories, or the data may be stacked temporally.

Once the training pairs 608 have been generated, a portion of the training pairs 608 may be assigned to a test dataset, as test pairs 618. The test dataset may be used to prevent overfitting, whereby patient LOS prediction model 602 may learn to map features specific to samples of the training set that are not present in the test set. In some embodiments, the training pairs 608 may be randomly assigned to either the training dataset or the test dataset in a pre-established proportion. For example, 90% of the training pairs 608 generated may be assigned to the training dataset, and 10% of the training pairs 608 generated may be assigned to the test dataset. In other embodiments, different proportions of training pairs 608 may be assigned to the training dataset and the test dataset. As a non-limiting example, the number of training pairs 608 used may be 10,000, and the number of test pairs 618 used may be 1000. It should be appreciated that the examples provided herein are for illustrative purposes, and the training pairs 608 may be assigned to the training dataset or the test dataset via a different procedure and/or in a different proportion without departing from the scope of this disclosure. In some embodiments, a training data set, test data set, and validation data set may be generated, for example, based on randomly selected patients clustered based on various factors.

LOS prediction model training system 600 may be implemented to train patient LOS prediction model 602 to learn to predict the actual LOS 612 of the patient. Patient LOS prediction model 602 may be configured to receive training pairs 608 from the training module 606, where data vector 610 and the corresponding actual LOS 612 are inputted into patient LOS prediction model 602. Patient LOS prediction model 602 may output a predicted LOS of the patient based on the data vector 610. Patient LOS prediction model 602 may then iteratively adjust one or more parameters of patient LOS prediction model 602 in order to minimize a loss function (e.g., based on a difference between the predicted LOS and actual LOS 612), until an error rate decreases below a first threshold error rate.

LOS prediction model training system 600 may include a validator 620 that validates a performance of patient LOS prediction model 602. Validator 620 may take as input a trained or partially trained patient LOS prediction model 602 and a test dataset of test pairs 618. If the error rate of the trained or partially trained patient LOS prediction model 602 on the test dataset of test pairs 618 decreases below a second threshold error rate, the performance of the trained or partially trained patient LOS prediction model 602 may be validated, whereby a training stage of the trained or partially trained patient LOS prediction model 602 may end.

For example, a partially trained patient LOS prediction model 602 of LOS prediction model training system may be validated with a test dataset of 50 test pairs 618, where each of the 50 test pairs 618 comprises a data vector 610 of a historical patient and an actual LOS 612 of the historical patient. Validator 620 may feed data vector 610 and actual patient LOS 612 into the partially trained patient LOS prediction model 602 and receive a predicted LOS as an output. Validator 620 may then compare the predicted LOS with the actual LOS 612. If an error between the predicted LOS and the actual LOS 612 is below the threshold error, the partially trained patient LOS prediction model 602 may be validated. After validation, a trained patient LOS prediction model 622 may be used to predict an LOS of a new patient based on patient data of the new patient, as described below in reference to FIG. 6B.

FIG. 6B shows a deployment diagram 650 of trained patient LOS prediction model 622 of FIG. 6A in use during deployment within a patient discharge date prediction system 654, which may be a non-limiting example of patient discharge date prediction system 100 of FIG. 1. Trained patient LOS prediction model 622 may be used to predict a LOS of a current patient of a hospital based on patient data of the patient. Validated patient LOS prediction model 622 may be included within an inference module 652 (e.g., inference module 212 of FIG. 2) of patient discharge date prediction system 654. Inference module 652 may also include instructions for deploying validated patient LOS prediction model 622 to generate a predicted LOS of the patient.

During operation of the patient discharge date prediction system 654, a set of current patients 656 may be selected for generating discharge date predictions. For example, as described above in reference to FIG. 3, the set of current patients 656 may be a group of patients being attended to at a hospital unit selected by a care provider via UI 300. The set of current patients 656 includes a plurality of individual patients 658, where each patient 658 is represented by a data vector 660 (e.g., data vector 552) generated, for example, in the manner described in FIG. 5B.

For each patient 658 of the set of current patients 656, a corresponding data vector 660 may be inputted into validated patient LOS prediction model 622, to output an LOS prediction 662 for the patient 658. For example, a first data vector 660 of a first patient 658 may be inputted into validated patient LOS prediction model 622 to generate a first LOS prediction for the first patient 658; a second data vector 660 of a second patient 658 may be inputted into validated patient LOS prediction model 622 to generate a second LOS prediction for the second patient 658; and so on, until an LOS prediction 662 has been generated for each patient 658 of the set of current patients 656. The patient discharge date prediction system 654 may then generate predicted discharge dates for each patient 658 of the set of current patients 656 based on the LOS predictions 662. Each predicted discharge date of each patient 658 may be used to generate a corresponding predicted discharge date window, based on a confidence level selected by the care provider. The patient discharge date prediction system 654 may then display a predicted discharge date window element indicating the predicted discharge date window in a UI of patient discharge date prediction system 654 (e.g., UI 300).

Figure 7:
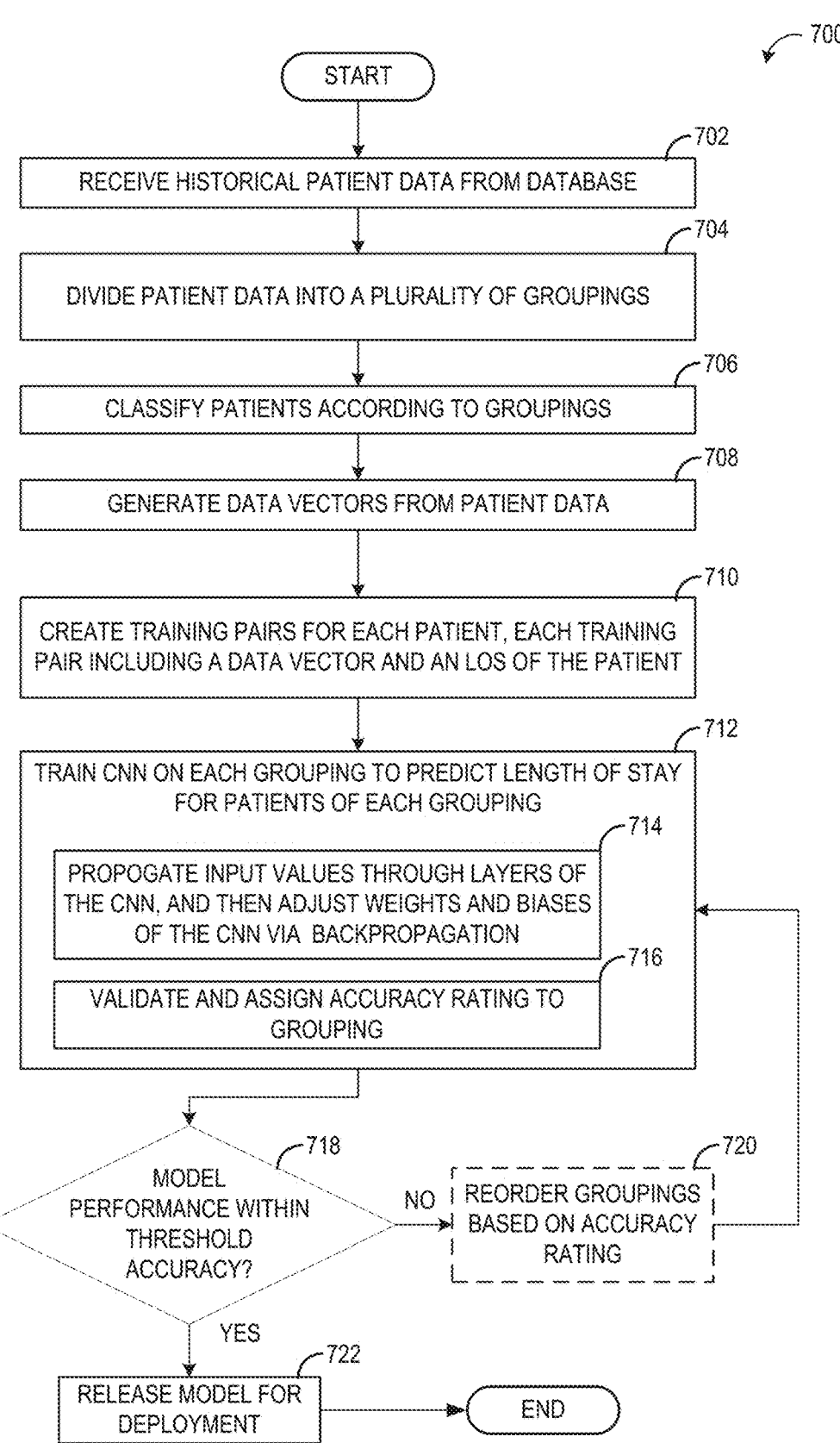
FIG. 7 shows a flowchart illustrating an exemplary method for training a CNN-based LOS prediction model to predict a length of stay for a patient, in accordance with an aspect of the disclosure.

Referring now to FIG. 7, a flowchart of an exemplary method 700 is shown for training a CNN-based patient LOS prediction model, such as patient LOS prediction model 602 of FIG. 6A, to predict a length of stay of a patient at one or more hospitals of a hospital network. Method 700 may be implemented as part of the LOS prediction model training system 600 of FIG. 6A. In an embodiment, one or more operations of method 700 may be stored in non-transitory memory and executed by a processor, such as the non-transitory memory 206 and processor 204 of patient discharge date prediction system 220 of FIG. 2.

The patient LOS prediction model may be trained using a training dataset comprising sets of input/target training pairs (e.g., training pairs 608). Each training pair of the input/target training pairs may include a data vector of a patient, and an actual LOS (e.g., ground truth) of the patient.

Method 700 begins at operation 702, where method 700 includes receiving historical patient data from one or more databases of the hospital network (e.g., computer systems and databases 230 of FIG. 2).

At 704, method 700 includes dividing the historical patient data into a plurality of groupings. In various embodiments, the groupings may be based on length of stay information in the historical patient data. For example, if the historical patient data includes patients with a length of stay ranging from one day to 90 days, then the 90 days may be divided into nine different 10 day groupings. A first ten-day grouping may include any patients with an LOS between one day and 10 days; a second grouping may include any patients with an LOS between 10 days and 20 days; a third grouping may include patients with an LOS between 20 days and 30 days; and so on. A number of groupings into which the historical patient data is divided may depend on a homogeneity of the historical patient data with respect to length of stay. For example, if the LOS's of patients of the historical patient data fall within a short range, a small number of groupings may be used, and if the LOS is of patients of the historical patient data fall within a wide range, a larger number of groupings may be used. Other factors may additionally be used to determine the number of groupings into which the historical patient data is divided. In some cases, a number of patients within each grouping may be used to determine a feasibility of using the grouping for training/validation.

In other embodiments, the groupings may be based partially or totally on factors other than length of stay. For example, a clustering algorithm, or a machine learning or deep learning algorithm may be used to identify groupings into which the patients cluster based on patient data and/or other data.

At 706, method 700 includes classifying patients according to the groupings. In various embodiments, each patient of the historical patient data may be assigned a grouping depending on the LOS of the patient. For example, a first set of patients having a short LOS may be assigned to a first grouping; a second set of patients having a longer LOS than the first set of patients may be assigned to a second grouping; a third set of patients having a longer LOS than the second set of patients may be assigned to a third grouping; and so on. In embodiments, where the groupings are generated based on the clustering algorithm or machine learning or deep learning algorithm, each patient of the historical patient data may be assigned a grouping based on the patient data used to generate the groupings.

At 708, method 700 includes generating data vectors for each patient of the historical patient data. The data vectors may be the same as or similar to data vector 552 described above in reference to FIG. 5B.

At 710, method 700 includes creating training pairs for each patient, each training pair including a data vector of the patient as input data, and an LOS of the patient as ground truth data. In some embodiments, the training set may be stored in a training module of an image processing system, such as the training module 210 of patient discharge date prediction system 220 of FIG. 2. In some embodiments, the data vectors may be generated by a dataset generator of the training module, such as dataset generator 616 of FIG. 6A.

At 712, method 700 includes training the CNN on each grouping to predict an LOS of each patient of each grouping. During training of the CNN, each data vector of a training pair of a grouping may be inputted into the CNN (e.g., into an input layer of the CNN) to generate a predicted LOS of the patient corresponding to the data vector as an output. For example, patient data (e.g., data vectors) of a first grouping may be inputted into the CNN in a first training step. After training on the first grouping has completed, patient data of a second grouping may be inputted into the CNN in a second training step, and so on.

At 714, training the CNN on each grouping includes propagating input values of the data vector through layers of the network, from the input layer, through one or more hidden layers, until reaching an output layer of the CNN. Propagating input values of the data vector through layers of the network may include performing convolutions and/or pooling operations on the data vector.

For example, in an embodiment, the CNN may have two convolutional layers, a fully connected layer, and an output layer. In some embodiments, pooling layers may be included between a first convolutional layer and a second convolutional layer, and/or between the second convolutional layer and the fully connected layer. Convolutions may be performed on the input values at the first convolutional layer of the CNN, resulting in a first set of feature maps. The first set of feature maps outputted by the first convolutional layer may be pooled at a first pooling layer, resulting in pooled feature maps. A first set of computed values of the pooled feature maps outputted by the first pooling layer may be inputted into the second convolutional layer. Convolutions may be performed on the first set of computed values at the second convolutional layer, resulting in a second set of feature maps. The second set of feature maps outputted by the second convolutional layer may be pooled at a second pooling layer, resulting in a second set of pooled feature maps. A second set of computed values of the second set of pooled feature maps outputted by the second pooling layer may be inputted into a fully connected layer of the CNN, which may generate one or more output values of the CNN at an output layer. In various embodiments, the one or more output values may include an encoding of an LOS of the patient, as described above in reference to FIG. 6A. For example, the output may be a number of days that the patient is predicted to stay at the hospital.

In some embodiments, outputs of the first convolutional layer, the second convolutional layer, and the fully connected layer may be modified by an activation function prior to being inputted into the first pooling layer, the second pooling layer, and the output layer, respectively. For example, the activation function may be a rectified linear activation function (ReLU).

After propagating the input values of the data vector through the layers of the CNN, a plurality of weights and biases at each layer of the CNN may be adjusted via backpropagation. In various embodiments, adjusting the plurality of weights and biases of the CNN may include calculating a difference between the output of the CNN and the actual LOS of the patient inputted into the CNN as a target ground truth value along with the data vector. The plurality of weights and biases of the CNN may be adjusted based on the difference between the output and the target ground truth from a relevant training pair. The difference (or loss), as determined by a loss function, may be backpropagated through the CNN to update weights of the convolutional layers. In some embodiments, backpropagation of the loss may be carried out according to a gradient descent algorithm, wherein a gradient of the loss function (a first derivative, or approximation of the first derivative) is determined for each weight and bias of the CNN. Each weight (and bias) of the CNN may be updated by adding the negative of the product of the gradient determined (or approximated) for the weight (or bias) with a predetermined step size. The backpropagation may comprise computing the gradient one layer at a time, iterating backward from the last layer to the first layer. It will be noted that method 700 may be repeated until the weights and biases of the CNN converge, or the rate of change of the weights and/or biases of the CNN for each iteration of method 700 are below a threshold rate of change.

At 716, training the CNN on each grouping further includes validating and assigning an accuracy rating to the grouping. In order to avoid overfitting, training of the CNN may be periodically interrupted to validate a performance of the CNN on a test set comprising test pairs, such as test pairs 618 of FIG. 6A. In one example, both the training pairs of the training set and the test pairs of the test set may be selected at random from a larger training dataset. In some embodiments, training of the CNN may end when the performance of the CNN on the test training pairs converges (e.g., when an error rate on the test set converges on a minimum value).

In some embodiments, after training the CNN on a grouping, an accuracy rating may be assigned to the grouping. For example, a first grouping including patients with an LOS within a first range may be assigned a first accuracy rating; a second grouping including patients with an LOS within a second range may be assigned a second accuracy rating; a third grouping including patients with an LOS within a third range may be assigned a third accuracy rating; and so on. The accuracy rating of each grouping may represent an accuracy of the CNN in predicting an LOS within the range associated with each grouping. For example, the CNN may have a high accuracy in predicting patient LOS for patients that are typically discharged around 2-3 days after they are admitted, but the CNN may have a lower accuracy in predicting patient LOS for patients that are typically discharged 10 days after they are admitted. The CNN may have an even lower accuracy in predicting patient LOS for patients that are typically discharged after several months. The accuracy of the CNN for different LOS ranges may be advantageously used to increase an accuracy of a predicted discharge date window of the patient, as described in greater detail below in reference to FIG. 8.

At 718, method 700 includes determining whether an overall performance of the CNN (e.g., across a plurality of groupings) is within a threshold accuracy. If at 718 it is determined that the CNN-based model is within the threshold accuracy, method 700 proceeds to 722. At 722, method 700 includes releasing the CNN-based model for deployment, and method 700 ends. If at 718 it is determined that the CNN-based model is not within the threshold accuracy, method 700 proceeds to 720.

At 720, method 700 may include reordering the groupings based on the accuracy rating ratings assigned at 716. For example, in a first training stage, training of the CNN on each grouping may be performed in a first order. For example, the first order may be based on an LOS range of each grouping, where a first grouping used to train the CNN corresponds to a first LOS range; a second grouping used to train the CNN corresponds to a second LOS range, where the second LOS range is longer than the first LOS range; and a third grouping used to train the CNN corresponds to a third LOS range, where the third LOS range is longer than the second LOS range. After the first training step has completed, to improve a performance of the CNN, the groupings may be reordered according to a new order based on a relative accuracy of the first, second, and third groupings. For example, the CNN may predict an LOS of patients in the second LOS range with the highest accuracy; the CNN may predict an LOS of patients in the first LOS range with a next highest accuracy; and the CNN may predict an LOS of patients in the third LOS range with a next highest accuracy. Based on the relative accuracies of the CNN, the groupings may be reordered such that the grouping associated with the second LOS range is first in the new order; the grouping associated with the first LOS range is second in the new order; and the grouping associated with the third LOS range is third in the new order. After reordering the groupings based on the accuracy ratings, method 700 may proceed back to 712, where the CNN may be retrained on each grouping in accordance with the new order.

In some embodiments, the CNN may be used to cluster similar patients together into new groupings, which may be used for further training.

By retraining the CNN in accordance with the new order of groupings, an overall accuracy of the CNN may be increased, where LOS's of new patient data vectors are predicted by the CNN with greater accuracy. Additionally, after retraining the CNN on each grouping in accordance with the new order, the relative accuracy of the CNN on the different LOS ranges may change. If the relative accuracy of the CNN on the different LOS ranges changes, the groupings may be once again reordered, and the CNN retrained on the groupings in the new order. In this way, the CNN may be trained iteratively and/or repeatedly to prioritize increasing an accuracy of the CNN on the groupings for which the CNN is most accurate.

In other embodiments, a different order of groupings may be used. For example, at 720, method 700 may include reordering the groupings in an increasing order of accuracy, where a first grouping of the order is a grouping on which the CNN is least accurate, followed by groupings on which the CNN is progressively more accurate. The CNN may then be retrained based on the new order, where the CNN may be trained iteratively and/or repeatedly to prioritize increasing and accuracy of the CNN on the groupings for which the CNN is least accurate.

Figure 8:
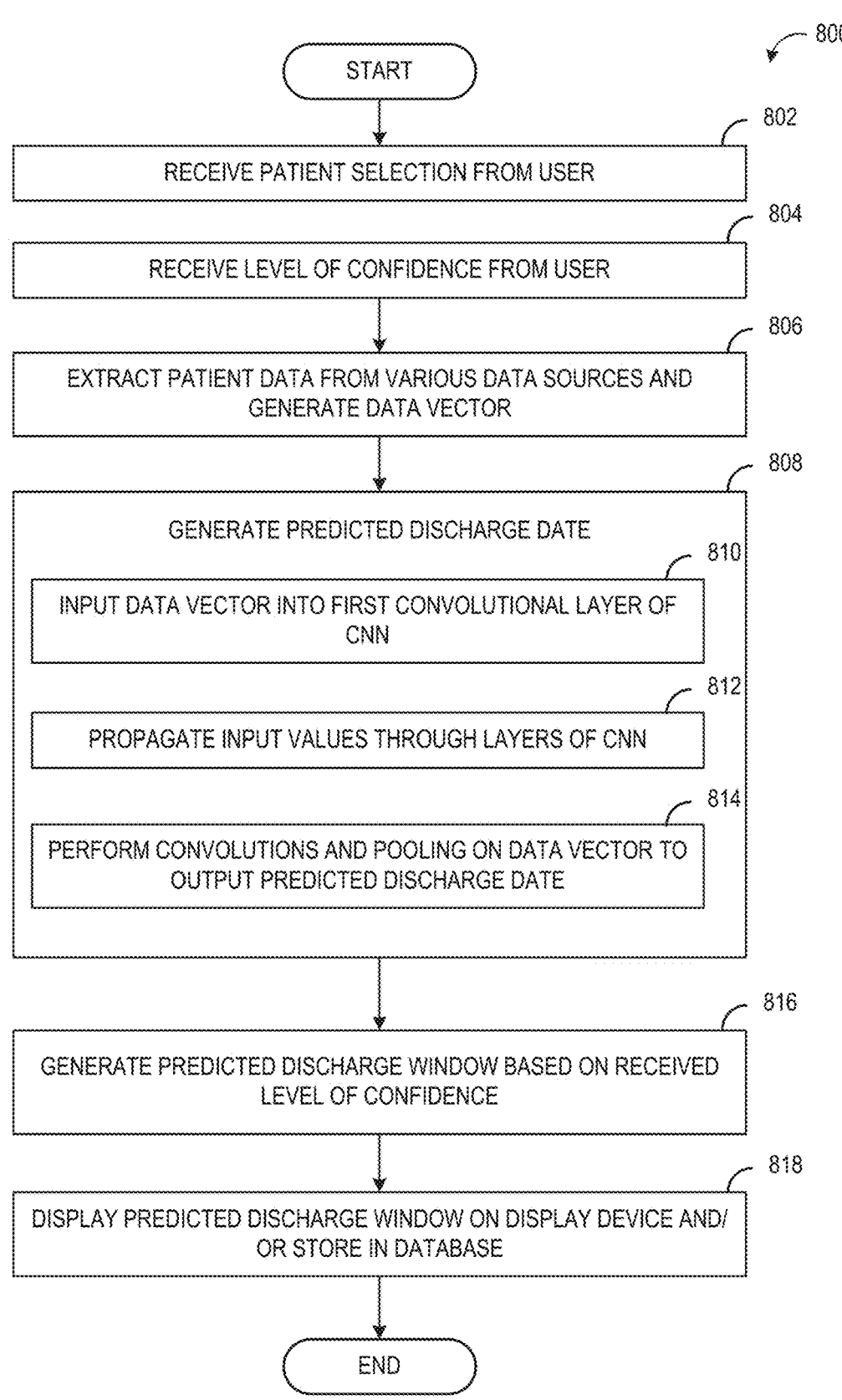
FIG. 8 shows a flowchart illustrating an exemplary method for deploying a trained CNN-based LOS prediction model to generate a predicted length of stay for a patient, in accordance with an aspect of the disclosure.

Referring now to FIG. 8, a method 800 is shown for predicting patient discharge date windows for a selected plurality of patients, according to an embodiment of the disclosure. Method 800 may be carried out by a patient discharge date prediction system, such as patient discharge date prediction system 220 of FIG. 2, according to instructions stored in a memory (e.g., non-transitory memory 206) of the patient discharge date prediction system, which may be executed by a processor (e.g., processor(s) 204) of the patient discharge date prediction system. The patient discharge window predictions may be made using a patient LOS prediction model, such as patient LOS prediction model 102 of FIG. 1, which may predict a length of stay of a patient based on patient data. The patient LOS prediction model may be a CNN-based model trained as described in reference to LOS prediction model training system 600 of FIG. 6A, and deployed as described in relation to deployment diagram 650 of FIG. 6B.

Method 800 begins at operation 802, where method 800 includes receiving a selection of patients for whom to predict the discharge date windows. In some embodiments, the patient discharge date prediction system may be hosted on a server (e.g., of the healthcare organization) and accessible to a plurality of hospitals over a network via a patient management application. A user (e.g., a care provider) may enter in a name of a hospital or select a hospital from a list of hospitals into a UI of the patient management application (e.g., UI 300) in order to indicate a selection of patients associated with the hospital. In other embodiments, a relevant hospital may automatically be selected based on a pre-defined configuration file created during a setup stage of the patient discharge date prediction system. The user may also enter in a name of a hospital unit to view a selection of patients within the hospital unit.

The selection of patients may be a total number of patients of the hospital or hospital unit, or a subset of the patients of the hospital or hospital unit. In other words, to reduce a processing time and receive results more quickly, the user may select a small group of patients of the hospital to quickly determine which patients of the small group of patients may be ready to be discharged, rather than wait for results from a larger group of patients. For example, the user may reduce a number of patients to request discharge window predictions for by using one or more of the filters described in reference to UI 300 of FIG. 3. In other examples, a discharge window prediction may be generated for each patient in the hospital unit, and a selected subset of the discharge window predictions may be displayed via the user interface, based on the filtering/user selections described above.

At 804, method 800 includes receiving a desired level of confidence of the discharge window predictions from the user. The desired level of confidence may reflect an estimated level of confidence of the patient discharge date prediction system that the patient may be discharged within the predicted discharge date window. For example, if the desired confidence level is high (e.g., 80%), the length of the discharge window may be extended to include a wider range of dates, to achieve the desired level of confidence that the patient may be discharged within the discharge window. Alternatively, if the desired confidence level is lower (e.g., 50%), the length of the discharge window may be reduced to include a narrower range of dates. If the desired confidence level is very low (e.g., 10%), the predicted discharge date window may be the predicted discharge date.

In some embodiments, the desired level of confidence may be selected by the user, for example, via a menu displayed in the UI of the patient management application. The desired confidence level may also be pre-configured in the patient discharge date prediction system by an administrator of the hospital or the patient discharge date prediction system. For example, the pre-configured confidence level may be based on administrative guidelines of the hospital or hospital network.

At 806, method 800 includes extracting patient data corresponding to the selected patients from various data sources and generating a data vector representing the patient data. The data vector may include one or more encodings of the patient data, as described above in reference to FIG. 5B.

In various embodiments, the patient data may be retrieved from one or more EHR and/or other computer systems of the hospital and/or the healthcare organization, such as computer systems and databases 230 of FIG. 2. The other computer systems may include a local monitoring application of the hospital used to make routine measurements (e.g., current vital signs) or tests of the patient.

In some embodiments, a portion of a comprehensive set of patient data of the patient may be extracted, and other portions of patient data may not be extracted. For example, a first set of patient data may be a comprehensive set of data of the patient, and the first set of patient data may be stored across a plurality of computer systems (e.g., EHR systems) and/or databases of a healthcare system. Out of the first set of patient data, a second, smaller set of patient data (e.g., a subset) may be retrieved, where the second, smaller set of patient data is patient data determined by the patient discharge date prediction system to be most relevant to a patient discharge.

In some embodiments, vital signs or clinical markers may be retrieved from a single source, such as a single EHR system, where the patient discharge window prediction module may retrieve a plurality of records of the vital sign or clinical marker and select a most recent vital sign or clinical marker from the plurality of records. Further, the patient discharge window prediction module may analyze the plurality of records to determine one or more trends in vital signs or clinical markers. In some examples, the patient discharge date prediction system may receive a secure data feed from the EHR that includes the patient parameters (e.g., vital signs, ventilation status, and care provider-entered information such as Glasgow coma score, etc.) for the patient. By obtaining the patient parameters from a single source on a semi-continuous feed (e.g., updated every 10, 15, or 30 seconds), the efficiency of the patient discharge date prediction system may be improved by reducing processing demands and network traffic associated with obtaining the patient parameters from multiple sources and/or requesting the patient parameters each time a discharge window prediction is made. In some examples, the patient discharge date prediction system may map specific feeds for each data source from the EHR using an API.

At 808, method 800 includes generating a predicted discharge date for each patient of the selection of patients. At 810, generating the predicted discharge date for each patient includes inputting each data vector of each patient of the selected patients into the CNN-based LOS prediction model. Specifically, each data vector may be inputted into a first convolutional layer of a CNN of the CNN-based LOS prediction model. At 812, generating the predicted discharge date for each patient includes propagating input values of the data vectors through layers of the network, from the input layer, through one or more hidden layers, until reaching an output layer of the CNN, as described above in reference to method 700 of FIG. 7. At 814, generating the predicted discharge date for each patient may include performing convolutions and/or pooling operations on the data vector to generate an output of the CNN, where the output of the CNN includes a predicted discharge date of the patient.

At 816, method 800 includes generating a discharge window prediction for each patient of the selection of patients from the predicted discharge date outputted by the CNN-based LOS prediction model. In various embodiments, the discharge window prediction for each patient may be based on the level of confidence received from the user (or pre-configured) at 804. The discharge window prediction may be a date range during which the discharge date prediction system predicts the patient will be discharged, within a threshold probability, where the threshold probability is based on the level of confidence.

In some embodiments, the discharge window prediction may include a number of days surrounding the predicted discharge date, where the number of days is a function of the level of confidence. For example, if the desired level of confidence of the discharge date prediction system in the predicted discharge date window is low, the discharge window prediction may be a date range including a first small number of days prior to the predicted discharge date, and a second small number of days after the predicted discharge date. In various embodiments, the first small number may be the same as the second small number. Alternatively, if the desired level of confidence of the discharge date prediction system in the predicted discharge date window is high, the discharge window prediction may be a date range including a first, larger number of days prior to the predicted discharge date, and a second, larger number of days after the predicted discharge date, where the first, larger number may be the same as the second, larger number.

In other embodiments, the discharge window prediction may include a number of days surrounding the predicted discharge date, where the number of days is based partly on the level of confidence and partly on other information considered or generated by the discharge date prediction system. For example, in some embodiments, the CNN of the CNN-based LOS prediction model may include an additional output, where the additional output may indicate an estimated probability of the predicted LOS being accurate. In other embodiments, the predicted discharge date window may be partially based on a classification of the LOS of each patient. For example, an accuracy of the CNN-based LOS prediction model in predicting a discharge date of a patient may depend on a length of the LOS, as described above in reference to method 700 of FIG. 7. If a predicted LOS of a patient is associated with a classification with a high degree of accuracy, the predicted discharge date window may be adjusted to a more narrow range of dates. Alternatively, if the predicted LOS of a patient is associated with a classification with a low degree of accuracy, the predicted discharge date window may be adjusted to a wider range of dates.

At 818, method 800 includes displaying predicted discharge date window elements indicating the predicted discharge date windows of the selected patients on the display screen of the patient discharge date prediction system (e.g., of the patient management application). The predicted discharge date window element may be presented on the screen in a UI of the patient discharge date prediction system, for example, as described in reference to FIG. 3 above. The patients may be displayed in a list on the screen in a predetermined order, based on user-selected criteria and/or guidelines of the hospital. In some embodiments, the predicted discharge date window element of a patient may be displayed in a row (or column) corresponding to the patient and identified by a patient identifier (e.g., a name, ID, etc.). In other embodiments, displaying the predicted discharge date window elements of the selected patients on the display screen may include ranking the patients displayed on the display screen by discharge window prediction (e.g., displayed in a different order for ease of use). For example, one discharge window prediction may be earlier than another discharge window prediction, where the patient discharge date prediction system may display patients that are predicted to be discharged first (e.g., at a top of a list of discharge window predictions displayed on the display screen), followed by patients who may be discharged later, and with patients predicted to be discharged after a longer time frame towards or at the bottom of the list. In this way, a care provider may view at a glance a number of patients that may be discharged soon, or within a desired time frame, to free up resources of the hospital.

In some embodiments, the user may enter a user input to a predicted discharge date window element, such as a mouse or touch hover, or a mouse click or touch input, in order to view additional information associated with the discharge window prediction. If the user has selected a discharge window prediction or element, additional information may be displayed based on the input. Displaying the additional information may include displaying a pop-up display based on the user input. When a user selects a predicted discharge date window element for a patient, information relating to a discharge of the patient may be displayed. For example, in one embodiment, the predicted discharge date window element may be a compressed view that displays a predicted discharge date, and the discharge window may be displayed when the user hovers over the predicted discharge date window element. In another embodiment, an earliest discharge date of a predicted discharge date window may be displayed when the user hovers over the predicted discharge date window element.

Further, the information relating to the discharge patient may be displayed when the user selects the predicted discharge date window element while the patient discharge date prediction system is in an unlaunched state. For example, the patient management application may be accessible to the user when the patient discharge date prediction system is not operating. The user may request to view patient discharge date window predictions of a selection of patients, whereby for each selected patient, a most recently predicted discharge date window may be displayed in the patient management application. For example, the most recently predicted discharge date window may have been generated during a previous operation of the patient discharge date prediction system (e.g., on a previous day). Patient information available at the time when the most recently predicted discharge date window was generated may be stored in the patient management application, such that the patient information may be displayed in the UI in response to the user selecting a discharge date prediction element of the UI. For example, when the user hovers over the predicted discharge date window element, an earliest discharge date of a predicted discharge date window may be displayed. If the user selects the earliest discharge date, additional patient data related to the predicted discharge date window may be displayed in the UI (e.g., via a pop-up window).

In addition to displaying the predicted discharge date window elements representing the discharge window predictions on the display screen, the discharge window predictions may be stored in a database of the hospital or hospital network (e.g., computer systems and databases 230 of FIG. 2).

Thus, the systems, methods, and graphical user interfaces provided herein may improve the accuracy and timeliness of patient discharges for high-demand, high-resource hospitals and/or hospital units. By establishing a system that automatically receives data from all EHRs in real time or near real time, aggregates that information regardless of data format, and periodically updates a GUI as data is received, the approach of the disclosure allows care providers to make informed decisions based on when patients may be discharged, thereby improving patient care.

In contrast, in prior systems when a care provider attempted to determine when a patient would be ready to discharge, errors could be made due to delays in individual care providers obtaining all desired parameters for accurately predicting patient discharge dates. For example, a patient's condition may have improved to the point where the patient would be ready for a discharge, but limited care provider resources may result in the patient being kept in the hospital for an additional 12, 24, or more hours, thereby utilizing hospital resources unnecessarily. The methods and systems solve this problem by providing specific, dynamically updating patient discharge window predictions, which can be selectively adjusted to indicate a greater or lesser degree of confidence in the discharge date prediction system's accuracy. In this way, the approach described herein provides an improvement to the capability of the healthcare system as a whole. The disclosure provides a specific way of improving the capability of the healthcare system, by dynamically updating patient discharge window prediction lists. The disclosure further provides a specific improvement to the way computers operate by aggregating EHR data for multiple patients in one location and updating the patient discharge window predictions in real-time, which may obviate the need for users to have to navigate through multiple different data files, manually update information as availability changes, and so forth, thereby increasing the efficiency of the operation of the computer for the user.

Further, hospitals may not be configured to share patient discharge data in real-time, across different units of the hospital. Thus, prior methods of discharge readiness determination demanded manual collection of data (e.g., reading patient charts in person, discussing patient status with other care providers, visually inspecting each room for bed occupancy) and aggregation in a spreadsheet or other document, with updates also made manually. Systems were not available to automatically pull EHR data from multiple patients in multiple hospital units and then aggregate the pulled data into a visually clear format where healthcare decisions can be quickly made just by glancing at a GUI, as described in the embodiments herein.

The GUIs described herein provide a specific manner of displaying a limited set of information to a user (patient discharge date windows), rather than using conventional user interface methods to display a generic index on a computer, requiring the user to step through many layers of menu options to reach the desired data, or burying the desired data within all hospital data. Thus, the user experience with the computer may be improved and made more efficient.

Furthermore, by displaying a limited set of information via the discharge window predictions as described herein, operation of the computing device(s) that collect and render the data for display may be improved by reducing the processing demands of the computing device(s), thereby increasing the efficiency of the computing device(s). Further, in some examples the data is processed in real time and updates to the GUIs are made continuously as data is received, and therefore undue processing lags that may occur if updates were made at predefined discrete time points may be reduced, which may improve the efficiency of the computing device(s).

Via the disclosed patient discharge date prediction system, discharge window predictions for a patient may be displayed in a manner that is easy to visually parse and act on in a reduced amount of time. The discharge window predictions may be displayed via small graphical elements with minimal text, which may allow a large number of discharge window predictions to be included on the same screen. The patient information may be stored in different databases that would otherwise be accessed via individual interfaces, and by using the patient discharge date prediction system to aggregate the patient information, an amount of time taken to review relevant patient information to predict a discharge date of a patient may be reduced.

The technical effect of automatically generating discharge window predictions for patients of a hospital based on patient data using a length-of-stay prediction model is that resources of the hospital may be more efficiently managed to meet demands.

The disclosure also provides support for a method for a patient management system of a healthcare facility, comprising: receiving a selected confidence level from a user of the patient management system, predicting a date for discharging a patient of the healthcare facility based on a set of patient data of the patient, using a trained length of stay (LOS) prediction model, the LOS prediction model trained on historical patient data of the healthcare facility, predicting a discharge date window of the patient, based on the received confidence level, generating a predicted discharge date window element summarizing the predicted discharge date window in a user interface (UI) of the patient management system, and displaying the UI on a display device of the patient management system. In a first example of the method, the set of patient data of the patient is accessible from a plurality of sources communicably coupled to the patient management system, the plurality of sources distributed across one or more systems and/or databases communicatively coupled to a computer system of the healthcare facility via a network, including one or more Electronic Health Record (EHR) systems. In a second example of the method, optionally including the first example, the received confidence level is an estimated probability that a discharge date of the patient falls within the predicted discharge date window of the patient. In a third example of the method, optionally including one or both of the first and second examples, the historical patient data used to train the LOS prediction model includes destinations to which patients of the historical patient data were discharged, and predicting the date for discharging the patient using the trained LOS prediction model further comprises predicting a destination to which the patient will be discharged, and predicting the date for discharging the patient based partially on the predicted destination. In a fourth example of the method, optionally including one or more or each of the first through third examples, training the LOS prediction model on the historical patient data further comprises: grouping the historical patient data into a plurality of groupings based on LOS, classifying each patient of the historical patient data based on the groupings, generating a data vector for each patient, the data vector including patient data of the patient, and for each grouping, training the LOS prediction model on the data vectors of the patients of the grouping, using an LOS of the patients as ground truth values. In a fifth example of the method, optionally including one or more or each of the first through fourth examples, predicting the discharge date window of the patient based on the received confidence level further comprises determining an accuracy of the LOS prediction model on each grouping, and predicting the discharge date window of the patient based on the received confidence level and the accuracy of the LOS prediction model for the grouping to which the patient belongs. In a sixth example of the method, optionally including one or more or each of the first through fifth examples, generating the predicted discharge date window element summarizing the predicted discharge date window in the UI of the patient management system further comprises displaying the predicted discharge date window element in an integrated view of the UI, the integrated view including clinical information of a plurality of patients of the healthcare facility. In a seventh example of the method, optionally including one or more or each of the first through sixth examples, the clinical information of a plurality of patients is presented in rows of the UI, each row including clinical information of a single patient, and the rows are ordered based on each patient's predicted discharge date. In an eighth example of the method, optionally including one or more or each of the first through seventh examples, the predicted discharge date window element is a first discharge prediction element, arranged in the UI proximate a second discharge prediction element summarizing a geometric mean length of stay (GMLOS) for patients with a same condition as the patient, and a third discharge prediction element summarizing an expected discharge date (EDD), where the predicted discharge date window, the GMLOS, and the EDD are generated independently. In a ninth example of the method, optionally including one or more or each of the first through eighth examples, the set of patient data is updated asynchronously, and the discharge date of the patient is periodically predicted to generate real-time updates to the predicted discharge date window. In a tenth example of the method, optionally including one or more or each of the first through ninth examples, the predicted discharge date window element indicates the predicted discharge date, and responsive to the user selecting the predicted discharge date window element, an earliest predicted discharge date is displayed in the UI, the earliest predicted discharge date based on the received confidence level. In a eleventh example of the method, optionally including one or more or each of the first through tenth examples, in response to a current date being within the predicted discharge date window of the patient, displaying an alert in the UI. In a twelfth example of the method, optionally including one or more or each of the first through eleventh examples, the method further comprises: sending a notification to a care provider of the patient indicating one or more administrative tasks to be performed prior to discharging the patient.

The disclosure also provides support for a method for a patient discharge date prediction system, comprising: receiving, at the patient discharge date prediction system, a secure feed from one or more electronic health record databases of a hospital network, the secure feed including patient data of a plurality of patients, responsive to a first user input selecting a first hospital of the hospital network, displaying a graphical user interface (GUI) that displays, for each patient of the plurality of patients, a first predicted discharge date of the patient, where each first predicted discharge date is predicted based on a first set of patient data obtained from the secure feed, the first set of patient data selected based on the first hospital, and responsive to a second user input selecting a second hospital, displaying the GUI with a second predicted discharge date for the plurality of patients, where each second predicted discharge date is predicted based on a second set of patient data obtained from the secure feed, the second set of patient data selected based on the second hospital. In a first example of the method, the first set of patient data is different from the second set of patient data.

The disclosure also provides support for a patient discharge date prediction system, comprising: one or more processors, and memory storing instructions executable by the one or more processors to: receive, at the patient discharge date prediction system, a secure feed from one or more electronic health record databases of a hospital network, the secure feed including patient data of a plurality of patients, output, for display on a display device, a graphical user interface (GUI) that includes a predicted discharge date of each patient of the plurality of patients, the predicted discharge date predicted by a length of stay (LOS) prediction model based on the patient data of the patient included in the secure feed, the LOS prediction model trained on de-identified historical patient data of the one or more electronic health record databases. In a first example of the system, updated patient data is received in real time via the secure feed, and wherein the predicted date for discharging each patient is updated based on the updated patient data at either or both of a predetermined frequency and in response to the updated patient data received in real time exceeding a threshold amount of patient data. In a second example of the system, optionally including the first example, training the LOS prediction model on the de-identified historical patient data further comprises: assigning each patient of the de-identified historical patient data a classification based on an LOS of the patient and/or clustering techniques using machine learning or deep learning, for each classification: initializing the LOS prediction model with a set of initial parameters, training the LOS prediction model on patient data of patients sharing the classification, after training is completed, recording an accuracy of the LOS prediction model on the classification, ranking the classifications based on the recorded accuracies, reinitializing the LOS prediction model with the set of initial parameters, and retraining the LOS prediction model on patient data of the classifications in an order based on a rank of the classifications. In a third example of the system, optionally including one or both of the first and second examples, a predicted discharge date window is included in the GUI for each patient of the plurality of patients, the predicted discharge date window based on the predicted discharge date of the patient and a confidence level configurable by a user of the patient discharge date prediction system, the confidence level indicating an estimated probability that the patient will be discharged within the predicted discharge date window. In a fourth example of the system, optionally including one or more or each of the first through third examples, the system further comprises: predicting the discharge date window based on the predicted discharge date of the patient, the confidence level, and the accuracy of the LOS prediction model on the classification of the patient.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for a patient management system of a healthcare facility, comprising:
   receiving a selected confidence level from a user of the patient management system;
   receiving, via secure feeds from a plurality of electronic health record databases, patient data, wherein the patient data comprises temporal medical data in a plurality of different formats;
   encoding the received patient data into data vectors;
   predicting a date for discharging a patient of the healthcare facility based on the encoded data vectors using a trained length of stay (LOS) prediction model, the LOS prediction model trained on historical patient data of the healthcare facility, wherein the LOS prediction model is a convolution neural network (CNN), and wherein the LOS prediction model is trained by: dividing the historical patient data into a plurality of groupings based on length of stay ranges; classifying each patient of the historical patient data into one of the plurality of groupings; generating data vectors for each patient, each data vector encoding patient data of the respective patient; training the LOS prediction model sequentially on each grouping using the data vectors of patients in that grouping and actual length of stay values; determining an accuracy rating for each grouping based on prediction performance of the LOS prediction model for that grouping; reordering the plurality of groupings based on the accuracy ratings; and retraining the LOS prediction model on the reordered groupings;

predicting a discharge date window of the patient, based on the received confidence level and the trained LOS prediction model, wherein the discharge date window is a window of time greater than a single calendar day, wherein a width of the predicted discharge date window of the patient is at least partially based on the accuracy ratings;

generating a predicted discharge date window element summarizing the predicted discharge date window in a user interface (UI) of the patient management system;

displaying the UI on a display device of the patient management system;

detecting that a current date falls within the predicted discharge date window of the patient;

in response to detecting that the current date falls within the predicted discharge date window of the patient, automatically initiating discharge preparation workflows, wherein automatically initiating discharge preparation workflows comprises:

generating electronic notifications to care providers of the patient identifying administrative tasks required for discharge, wherein the administrative tasks include scheduling transportation arrangement and coordinating home care resource preparations; and automatically adjusting allocation of healthcare facility resources based on the predicted discharge; and dynamically updating the discharge preparation workflows in real-time based on new patient data received via the secure feed.

2. The method of claim 1, wherein the set of patient data of the patient is accessible from a plurality of sources communicably coupled to the patient management system, the plurality of sources distributed across one or more systems and/or databases communicatively coupled to a computer system of the healthcare facility via a network, including one or more Electronic Health Record (EHR) systems.

3. The method of claim 1, wherein the received confidence level is an estimated probability that a discharge date of the patient falls within the predicted discharge date window of the patient.

4. The method of claim 1, wherein the historical patient data used to train the LOS prediction model includes destinations to which patients of the historical patient data were discharged, and predicting the date for discharging the patient using the trained LOS prediction model further comprises predicting a destination to which the patient will be discharged, and predicting the date for discharging the patient based partially on the predicted destination.

5. The method of claim 1, wherein training the LOS prediction model on the historical patient data further comprises:

grouping the historical patient data into a plurality of groupings based on LOS;

classifying each patient of the historical patient data based on the groupings;

generating a data vector for each patient, the data vector including patient data of the patient; and for each grouping, training the LOS prediction model on the data vectors of the patients of the grouping, using an LOS of the patients as ground truth values.

6. The method of claim 5, wherein predicting the discharge date window of the patient based on the received confidence level further comprises determining an accuracy of the LOS prediction model on each grouping, and predicting the discharge date window of the patient based on the received confidence level and the accuracy of the LOS prediction model for the grouping to which the patient belongs.

7. The method of claim 1, wherein generating the predicted discharge date window element summarizing the predicted discharge date window in the UI of the patient management system further comprises displaying the predicted discharge date window element in an integrated view of the UI, the integrated view including clinical information of a plurality of patients of the healthcare facility.

8. The method of claim 7, wherein the clinical information of a plurality of patients is presented in rows of the UI, each row including clinical information of a single patient, and the rows are ordered based on each patient's predicted discharge date.

9. The method of claim 7, wherein the predicted discharge date window element is a first discharge prediction element, arranged in the UI proximate a second discharge prediction element summarizing a geometric mean length of stay (GMLOS) for patients with a same condition as the patient, and a third discharge prediction element summarizing an expected discharge date (EDD), where the predicted discharge date window, the GMLOS, and the EDD are generated independently.

10. The method of claim 7, wherein the set of patient data is updated asynchronously, and the discharge date of the patient is periodically predicted to generate real-time updates to the predicted discharge date window.

11. The method of claim 7, wherein the predicted discharge date window element indicates the predicted discharge date, and responsive to the user selecting the predicted discharge date window element, an earliest predicted discharge date is displayed in the UI, the earliest predicted discharge date based on the received confidence level.

12. The method of claim 1, wherein the patient data comprises patient parameters, wherein the patient parameters are received from a single source on a semi-continuous feed, and wherein in response to a current date being within the predicted discharge date window of the patient, displaying an alert in the UI.

13. A method for a patient discharge date prediction system, comprising:

receiving, at the patient discharge date prediction system, secure feeds from one or more electronic health record databases of a hospital network, wherein the secure feeds include medical images stored in Digital Imaging and Communications in Medicine (DICOM) format from a picture archiving and communication system (PACS), blood parameter reports stored in a first format different from the DICOM format, pathological reports stored in a second format different from the DICOM format and the first format, and patient monitoring data received from patient monitoring devices;

aggregating and encoding the medical images, blood parameter reports, pathological reports, and patient monitoring data into data vectors regardless of original data format;

receiving a selected confidence level from a user;

predicting, for each patient of a first set of patients associated with a first healthcare facility, a first predicted discharge date using a trained length of stay (LOS) prediction model based on the encoded data vectors, the trained LOS prediction model trained based on historical patient data;

predicting, for each patient of the first set of patients, a first predicted discharge date window based on the trained LOS prediction model, the encoded data vectors, and the selected confidence level;

predicting, for each patient of a second set of patients associated with a second healthcare facility, a second predicted discharge date using the LOS prediction model based on the encoded data vectors;

predicting, for each patient of the second set of patients, a second predicted discharge date window based on the trained LOS prediction model, the encoded data vectors, and the selected confidence level, wherein the first predicted discharge date window and the second predicted discharge date window are windows of time greater than a calendar day;

responsive to a first user input selecting the first healthcare facility, displaying a graphical user interface (GUI) that displays, for each patient of the first set of patients, the first predicted discharge date and the first predicted discharge date window of the patient; and responsive to a second user input selecting the second healthcare facility, displaying the GUI with the second predicted discharge date and the second predicted discharge date window for each patient of the second set of patients;

wherein the trained LOS prediction model is a convolution neural network (CNN) comprising two convolutional layers, a fully connected layer, an output layer, and pooling layers;

wherein the trained LOS prediction model is trained by propagating input values of the encoded data vector through the two convolutional layers, the pooling layers, the fully connected layer, and the output layer, and wherein propagating input values of the data vector through the layers of the CNN includes performing convolutions and/or pooling operations on the data vector;

wherein training the LOS prediction model comprises: dividing the historical patient data into a plurality of groupings based on length of stay ranges; classifying each patient of the historical patient data into one of the plurality of groupings;

generating data vectors for each patient, each data vector encoding patient data of the respective patient; training the LOS prediction model sequentially on each grouping using the data vectors of patients in that grouping and actual length of stay values; determining an accuracy rating for each grouping based on prediction performance of the LOS prediction model for that grouping; reordering the plurality of groupings based on the accuracy ratings; and retraining the LOS prediction model on the reordered groupings; and wherein a width of each of the first predicted discharge date window and the second predicted discharge date window is at least partially based on the accuracy ratings.

14. The method of claim 13, wherein the first set of patients is different from the second set of patients.

15. A patient discharge date prediction system, comprising:
  one or more processors; and memory storing instructions executable by the one or more processors to:
    receive, at the patient discharge date prediction system, a secure feed from one or more electronic health record databases of a hospital network, the secure feed including patient data of a plurality of patients;
    output, for display on a display device, a graphical user interface (GUI) that includes a predicted discharge date and a predicted discharge date window of each patient of the plurality of patients, the predicted discharge date predicted by a length of stay (LOS) prediction model based on the patient data of the patient included in the secure feed, the LOS prediction model trained on de-identified historical patient data of the one or more electronic health record databases, the predicted discharge date window a window of time greater than a calendar day and based on the predicted discharge date of the patient and a confidence level configurable by a user of the patient discharge date prediction system, the confidence level indicating an estimated probability that the patient will be discharged within the predicted discharge date window; and
    in response to a current date being within the predicted discharge date window of the patient, display an alert in the UI and send a notification to a care provider of the patient indicating one or more administrative tasks to be performed prior to discharging the patient;
  wherein the GUI comprises a first alternative view and second alternative view, wherein the first alternative view displays information in a fixed format that is not customizable by the user, and the second alternative view displays information in a variable format that is customizable by the user to hide columns, rows, sections, or elements, and wherein the second alternative view is displayed in response to the user selecting a toggle switch; and
  wherein the LOS prediction model is a convolution neural network (CNN), and wherein the LOS prediction model is trained by: dividing the de-identified historical patient data into a plurality of groupings based on length of stay ranges; classifying each patient of the de-identified historical patient data into one of the plurality of groupings; generating data vectors for each patient, each data vector encoding patient data of the respective patient; training the LOS prediction model sequentially on each grouping using the data vectors of patients in that grouping and actual length of stay values; determining an accuracy rating for each grouping based on prediction performance of the LOS prediction model for that grouping; reordering the plurality of groupings based on the accuracy ratings; and retraining the LOS prediction model on the reordered groupings, and wherein a width of the predicted discharge date window of the patient is at least partially based on the accuracy ratings.

16. The system of claim 15, wherein updated patient data is received in real time via the secure feed, and wherein the predicted date for discharging each patient is updated based on the updated patient data at either or both of a predetermined frequency and in response to the updated patient data received in real time exceeding a threshold amount of patient data.

17. The system of claim 15, wherein training the LOS prediction model on the de-identified historical patient data further comprises:

assigning each patient of the de-identified historical patient data a classification based on an LOS of the patient and/or clustering techniques using machine learning or deep learning;

for each classification:

initializing the LOS prediction model with a set of initial parameters;

training the LOS prediction model on patient data of patients sharing the classification;

after training is completed, recording an accuracy of the LOS prediction model on the classification;

ranking the classifications based on the recorded accuracies;

reinitializing the LOS prediction model with the set of initial parameters; and retraining the LOS prediction model on patient data of the classifications in an order based on a rank of the classifications.

18. The system of claim 15, further comprising predicting the discharge date window based on the predicted discharge date of the patient, the confidence level, and the accuracy of the LOS prediction model on the classification of the patient.

* * * * *